(12) United States Patent
Dickinson et al.

(10) Patent No.: US 11,446,170 B2
(45) Date of Patent: *Sep. 20, 2022

(54) MINIMALLY INVASIVE SURGICAL APPARATUS AND METHODS

(71) Applicant: LimFlow GmbH, Dresden (DE)

(72) Inventors: Robert Julian Dickinson, London (GB); Andrew Robert Pacey, Herts (GB); Martin Terry Rothman, Santa Rosa, CA (US); Ajay Kumar Jain, London (GB)

(73) Assignee: LimFlow Gmbh, Dresden (DE)

( * ) Notice: Subject to any disclaimer, the term of this patent is extended or adjusted under 35 U.S.C. 154(b) by 403 days.

This patent is subject to a terminal disclaimer.

(21) Appl. No.: 16/552,168

(22) Filed: Aug. 27, 2019

(65) Prior Publication Data

US 2020/0054469 A1  Feb. 20, 2020

Related U.S. Application Data

(63) Continuation of application No. 14/141,913, filed on Dec. 27, 2013, now Pat. No. 10,398,580, which is a
(Continued)

(30) Foreign Application Priority Data

Sep. 8, 2004  (GB) ..................... 0419954

(51) Int. Cl.
*A61B 5/00*  (2006.01)
*A61F 2/966*  (2013.01)
(Continued)

(52) U.S. Cl.
CPC .............. *A61F 2/966* (2013.01); *A61B 17/11* (2013.01); *A61B 17/2202* (2013.01);
(Continued)

(58) Field of Classification Search
CPC ..................... A61B 2017/00252; A61F 2/966
See application file for complete search history.

(56) References Cited

U.S. PATENT DOCUMENTS

| 3,848,579 A | 11/1974 | Villa-Real |
| 4,249,539 A | 2/1981 | Vilkomerson et al. |

(Continued)

FOREIGN PATENT DOCUMENTS

| AU | 2012258395 | 3/2013 |
| CN | 102083376 | 6/1944 |

(Continued)

OTHER PUBLICATIONS

Tang et al., "The effects of stent porosity on the endovascular treatment of intracranial aneurysms located near a bifurcation", J. Biomedical Science and Engineering, 2013, vol. 6, pp. 812-822.
(Continued)

*Primary Examiner* — Rajeev P Siripurapu
(74) *Attorney, Agent, or Firm* — Knobbe Martens Olson & Bear, LLP

(57) ABSTRACT

Apparatus and methods are described for performing percutaneous catheter-based interventional surgery. The apparatus comprises first and second devices that are located in adjacent body cavities, such as adjacent blood vessels, the first device being capable of transmitting a directional signal that can be received by the second device. The direction of the signal is correlated with the facility to direct therapy, such that improved accuracy in therapy placement is thereby achieved. Methods for treating patients utilising the means and apparatus are also provided.

19 Claims, 7 Drawing Sheets

Related U.S. Application Data continuation of application No. 11/662,128, filed as application No. PCT/GB2005/003480 on Sep. 8, 2005, now abandoned.

(51) Int. Cl.
*A61B 17/34* (2006.01)
*A61B 34/20* (2016.01)
*A61B 17/11* (2006.01)
*A61B 17/22* (2006.01)
*A61B 90/00* (2016.01)
*A61B 17/00* (2006.01)

(52) U.S. Cl.
CPC .......... *A61B 17/3478* (2013.01); *A61B 34/20* (2016.02); *A61B 2017/00252* (2013.01); *A61B 2017/1107* (2013.01); *A61B 2017/1139* (2013.01); *A61B 2017/22082* (2013.01); *A61B 2034/2051* (2016.02); *A61B 2034/2063* (2016.02); *A61B 2090/3782* (2016.02); *A61B 2090/3786* (2016.02); *A61B 2090/3788* (2016.02); *A61B 2090/3929* (2016.02)

(56) References Cited

U.S. PATENT DOCUMENTS

| | | |
|---|---|---|
| 4,560,374 A | 12/1985 | Hammerslag |
| 4,586,919 A | 5/1986 | Taheri |
| 4,655,746 A | 4/1987 | Daniels et al. |
| 4,739,760 A | 4/1988 | Chin et al. |
| 4,757,821 A | 7/1988 | Snyder |
| 4,768,508 A | 9/1988 | Chin et al. |
| 4,952,215 A | 8/1990 | Ouriel et al. |
| 5,047,041 A | 9/1991 | Samuels |
| 5,092,872 A | 3/1992 | Segalowitz |
| 5,203,777 A | 4/1993 | Lee |
| 5,234,450 A | 8/1993 | Segalowitz |
| 5,284,478 A | 2/1994 | Nobles et al. |
| 5,304,189 A | 4/1994 | Goldberg et al. |
| 5,352,232 A | 10/1994 | Cohen |
| 5,397,339 A | 3/1995 | Desai |
| 5,443,497 A | 8/1995 | Venbrux |
| 5,591,226 A | 1/1997 | Trerotola et al. |
| 5,601,580 A | 2/1997 | Goldberg et al. |
| 5,639,278 A | 6/1997 | Dereume et al. |
| 5,655,548 A | 8/1997 | Nelson et al. |
| 5,676,670 A | 10/1997 | Kim |
| 5,720,776 A | 2/1998 | Chuter et al. |
| 5,759,174 A | 6/1998 | Fischell et al. |
| 5,782,904 A | 7/1998 | White et al. |
| 5,792,056 A | 8/1998 | Prince |
| 5,797,920 A | 8/1998 | Kim |
| 5,800,522 A | 9/1998 | Campbell et al. |
| 5,824,071 A | 10/1998 | Nelson et al. |
| 5,830,222 A | 11/1998 | Makower |
| 5,830,224 A | 11/1998 | Cohn et al. |
| 5,843,171 A | 12/1998 | Campbell et al. |
| 5,897,495 A | 4/1999 | Aida et al. |
| 5,916,264 A | 6/1999 | von Oepen et al. |
| 5,938,697 A | 8/1999 | Killion et al. |
| 5,951,599 A | 9/1999 | McCrory |
| 5,976,178 A | 11/1999 | Goldsteen et al. |
| 6,007,544 A | 12/1999 | Kim |
| 6,015,405 A | 1/2000 | Schwartz et al. |
| 6,036,702 A | 3/2000 | Bachinski et al. |
| 6,068,638 A | 5/2000 | Makower |
| 6,071,292 A | 6/2000 | Makower et al. |
| 6,081,738 A | 6/2000 | Hinohara et al. |
| 6,099,542 A | 8/2000 | Cohn et al. |
| 6,099,559 A | 8/2000 | Nolting |
| 6,102,884 A | 8/2000 | Squitieri |
| 6,117,165 A | 9/2000 | Becker |
| 6,126,649 A | 10/2000 | VanTassel et al. |
| 6,159,225 A | 12/2000 | Makower |
| 6,159,238 A | 12/2000 | Killion et al. |
| 6,164,281 A | 12/2000 | Zhao |
| 6,165,185 A | 12/2000 | Shennib et al. |
| 6,186,972 B1 | 2/2001 | Nelson et al. |
| 6,190,353 B1 | 2/2001 | Makower et al. |
| 6,190,379 B1 | 2/2001 | Heuser et al. |
| 6,193,745 B1 | 2/2001 | Fogarty et al. |
| 6,193,763 B1 | 2/2001 | Mackin |
| 6,206,912 B1 | 3/2001 | Goldsteen et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,241,744 B1 | 6/2001 | Imran et al. |
| 6,251,116 B1 | 6/2001 | Shannib et al. |
| 6,254,610 B1 | 7/2001 | Darvish et al. |
| 6,280,388 B1 | 8/2001 | Koger et al. |
| 6,283,951 B1 | 9/2001 | Flaherty et al. |
| 6,283,983 B1 | 9/2001 | Makower et al. |
| 6,287,317 B1 | 9/2001 | Makower et al. |
| 6,287,336 B1 | 9/2001 | Globerman et al. |
| 6,298,261 B1 | 10/2001 | Rex |
| 6,302,875 B1 | 10/2001 | Makower et al. |
| 6,302,905 B1 | 10/2001 | Goldsteen et al. |
| 6,330,884 B1 | 12/2001 | Kim |
| 6,364,900 B1 | 4/2002 | Heuser |
| 6,375,615 B1 | 4/2002 | Flaherty et al. |
| 6,379,319 B1 | 4/2002 | Garibotto et al. |
| 6,432,127 B1 | 8/2002 | Kim et al. |
| 6,447,539 B1 | 9/2002 | Nelson et al. |
| 6,458,140 B2 | 10/2002 | Akin et al. |
| 6,464,665 B1 | 10/2002 | Heuser |
| 6,464,681 B1 | 10/2002 | Heuser |
| 6,464,709 B2 | 10/2002 | Shennib et al. |
| 6,475,170 B1 | 11/2002 | Doron et al. |
| 6,475,222 B1 | 11/2002 | Berg et al. |
| 6,475,226 B1 | 11/2002 | Belef et al. |
| 6,477,402 B1 | 11/2002 | Lynch et al. |
| 6,485,509 B2 | 11/2002 | Killion et al. |
| 6,491,707 B2 | 12/2002 | Makower |
| 6,508,824 B1 | 1/2003 | Flaherty et al. |
| 6,511,458 B2 | 1/2003 | Milo et al. |
| 6,511,491 B2 | 1/2003 | Grudem et al. |
| 6,517,558 B2 | 2/2003 | Gittings et al. |
| 6,536,949 B1 | 3/2003 | Heuser |
| 6,544,230 B1 | 4/2003 | Flaherty et al. |
| 6,554,842 B2 | 4/2003 | Heuser et al. |
| 6,561,998 B1 | 5/2003 | Roth et al. |
| 6,569,145 B1 | 5/2003 | Shmulewitz et al. |
| 6,569,193 B1 | 5/2003 | Cox et al. |
| 6,579,311 B1 | 6/2003 | Makower |
| 6,582,409 B1 | 6/2003 | Squitieri |
| 6,585,650 B1 | 7/2003 | Solem |
| 6,589,164 B1 | 7/2003 | Flaherty |
| 6,602,241 B2 | 8/2003 | Makower et al. |
| 6,610,087 B1 | 8/2003 | Zarbatany et al. |
| 6,613,081 B2 | 9/2003 | Kim et al. |
| 6,616,675 B1 | 9/2003 | Evard et al. |
| 6,638,293 B1 | 10/2003 | Makower et al. |
| 6,652,576 B1 | 11/2003 | Stalker |
| 6,655,386 B1 | 12/2003 | Makower et al. |
| 6,660,024 B1 | 12/2003 | Flaherty et al. |
| 6,669,709 B1 | 12/2003 | Cohn et al. |
| 6,669,723 B2 | 12/2003 | Killian et al. |
| 6,685,648 B2 | 2/2004 | Flaherty et al. |
| 6,685,671 B1 | 2/2004 | Oishi et al. |
| 6,685,716 B1 | 2/2004 | Flaherty et al. |
| 6,699,280 B2 | 3/2004 | Camrud et al. |
| 6,709,444 B1 | 3/2004 | Makower |
| 6,711,429 B1 | 3/2004 | Gilboa et al. |
| 6,719,781 B1 | 4/2004 | Kim |
| 6,726,677 B1 | 4/2004 | Flaherty et al. |
| 6,730,116 B1 | 5/2004 | Wolinsky et al. |
| 6,746,426 B1 | 6/2004 | Flaherty et al. |
| 6,746,464 B1 | 6/2004 | Makower |
| 6,824,549 B1 | 11/2004 | Chao |
| 6,858,037 B2 | 2/2005 | Penn et al. |
| 6,858,038 B2 | 2/2005 | Heuser |
| 6,863,684 B2 | 3/2005 | Kim et al. |

(56) References Cited

U.S. PATENT DOCUMENTS

| | | |
|---|---|---|
| 6,881,199 B2 | 4/2005 | Wilk et al. |
| 6,926,690 B2 | 8/2005 | Renati |
| 6,929,009 B2 | 8/2005 | Makower et al. |
| 6,945,949 B2 | 9/2005 | Wilk |
| 7,018,401 B1 | 3/2006 | Hyodoh et al. |
| 7,025,773 B2 | 4/2006 | Gittings et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,134,438 B2 | 11/2006 | Makower et al. |
| 7,137,962 B2 | 11/2006 | Gittings et al. |
| 7,159,592 B1 | 1/2007 | Makower et al. |
| 7,166,088 B2 | 1/2007 | Heuser |
| 7,179,250 B2 | 2/2007 | Heuser |
| 7,179,270 B2 | 2/2007 | Makower |
| 7,195,637 B2 | 2/2007 | Mika |
| 7,191,015 B2 | 3/2007 | Lamson et al. |
| 7,214,241 B2 | 5/2007 | Zarbatany et al. |
| 7,294,115 B1 | 11/2007 | Wilk |
| 7,300,459 B2 | 11/2007 | Heuser |
| 7,303,571 B2 | 12/2007 | Makower et al. |
| 7,316,655 B2 | 1/2008 | Garibotto et al. |
| 7,351,247 B2 | 4/2008 | Kupiecki et al. |
| 7,357,794 B2 | 4/2008 | Makower et al. |
| 7,374,567 B2 | 5/2008 | Heuser |
| 7,387,636 B2 | 6/2008 | Cohn et al. |
| 7,402,141 B2 | 7/2008 | Heuser |
| 7,407,506 B2 | 8/2008 | Makower |
| 7,578,828 B2 | 8/2009 | Gittings et al. |
| 7,578,829 B2 | 8/2009 | Goldsteen et al. |
| 7,582,108 B2 | 9/2009 | Hierlemann et al. |
| 7,606,615 B2 | 10/2009 | Makower et al. |
| 7,618,374 B2 | 11/2009 | Barnes et al. |
| 7,621,902 B2 | 11/2009 | Nita et al. |
| 7,628,768 B2 | 12/2009 | Faul et al. |
| 7,632,303 B1 | 12/2009 | Stalker et al. |
| 7,637,870 B2 | 12/2009 | Flaherty et al. |
| 7,648,517 B2 | 1/2010 | Makower et al. |
| 7,655,033 B2 | 2/2010 | Fearnot et al. |
| 7,670,329 B2 | 3/2010 | Flaherty et al. |
| 7,704,222 B2 | 4/2010 | Wilk et al. |
| 7,717,930 B2 | 5/2010 | Paul, Jr. et al. |
| 7,722,658 B2 | 5/2010 | Richter et al. |
| 7,722,663 B1 | 5/2010 | Austin |
| 7,722,664 B2 | 5/2010 | Zarbatany et al. |
| 7,729,738 B2 | 6/2010 | Flaherty et al. |
| 7,736,327 B2 | 6/2010 | Wilk et al. |
| RE41,448 E | 7/2010 | Squitieri |
| 7,749,239 B2 | 7/2010 | De Winter |
| 7,771,409 B2 | 8/2010 | Chang et al. |
| 7,780,719 B2 | 8/2010 | Killion et al. |
| 7,806,829 B2 | 10/2010 | Hauck |
| 7,846,172 B2 | 12/2010 | Makower |
| 7,849,860 B2 | 12/2010 | Makower et al. |
| 7,850,705 B2 | 12/2010 | Bachinski et al. |
| 7,892,246 B2 | 2/2011 | Akin et al. |
| 7,892,247 B2 | 2/2011 | Conston et al. |
| 7,914,492 B2 | 3/2011 | Heuser |
| 7,955,343 B2 | 6/2011 | Makower et al. |
| 7,966,057 B2 | 6/2011 | Macaulay et al. |
| 7,967,769 B2 | 6/2011 | Faul et al. |
| 8,048,016 B2 | 11/2011 | Faul et al. |
| 8,062,321 B2 | 11/2011 | Heuser et al. |
| 8,062,346 B2 | 11/2011 | Quigley et al. |
| 8,066,674 B2 | 11/2011 | Heuser |
| 8,075,580 B2 | 12/2011 | Makower |
| 8,083,708 B2 | 12/2011 | Flaherty et al. |
| 8,090,430 B2 | 1/2012 | Makower et al. |
| 8,109,947 B2 | 2/2012 | Berg et al. |
| 8,142,387 B2 | 3/2012 | Heise et al. |
| 8,172,861 B2 | 5/2012 | Fuller et al. |
| 8,197,499 B2 | 6/2012 | Gurtner et al. |
| 8,216,259 B2 | 7/2012 | Gurtner et al. |
| 8,226,592 B2 | 7/2012 | Brenneman et al. |
| 8,231,646 B2 | 7/2012 | Kassab et al. |
| 8,235,916 B2 | 8/2012 | Whiting et al. |
| 8,251,943 B1 | 8/2012 | Spencer et al. |
| 8,282,591 B2 | 10/2012 | Khan et al. |
| 8,343,087 B2 | 1/2013 | Formichi |
| 8,343,089 B2 | 1/2013 | Chang |
| 8,361,101 B2 | 1/2013 | Kassab |
| 8,414,516 B2 | 4/2013 | Chang |
| 8,439,963 B2 | 5/2013 | Dickinson et al. |
| 8,506,516 B2 | 8/2013 | Kassab et al. |
| 8,540,668 B2 | 9/2013 | Griffin et al. |
| 8,545,418 B2 | 10/2013 | Heuser |
| 8,551,032 B2 | 10/2013 | Faul et al. |
| 8,574,185 B2 | 11/2013 | Faul et al. |
| RE44,639 E | 12/2013 | Squitieri |
| 8,636,791 B1 | 1/2014 | Raju et al. |
| 8,652,084 B2 | 2/2014 | Akingba |
| 8,727,988 B2 | 5/2014 | Flaherty et al. |
| 8,747,344 B2 | 6/2014 | Khan |
| 8,747,345 B2 | 6/2014 | Salloum |
| 8,753,366 B2 | 6/2014 | Makower et al. |
| 8,771,305 B2 | 7/2014 | Shriver |
| 8,784,474 B2 | 7/2014 | Sargent, Jr. |
| 8,808,358 B2 | 8/2014 | Khoury |
| 8,815,278 B2 | 8/2014 | Roorda |
| 8,858,490 B2 | 10/2014 | Chou et al. |
| 8,858,579 B2 | 10/2014 | Suyker et al. |
| 8,870,805 B2 | 10/2014 | Chang |
| 8,888,733 B2 | 11/2014 | Kassab |
| 8,894,681 B2 | 11/2014 | Kassab |
| 8,900,115 B2 | 12/2014 | Bolling et al. |
| 8,905,962 B2 | 12/2014 | Asano et al. |
| 8,915,934 B2 | 12/2014 | Nielsen et al. |
| 8,926,545 B2 | 1/2015 | Brenneman et al. |
| 8,945,039 B2 | 2/2015 | Kassab |
| 8,951,222 B2 | 2/2015 | Tarlian, Jr. et al. |
| 8,968,230 B2 | 3/2015 | Kassab |
| 8,979,786 B2 | 3/2015 | Kassab |
| 9,017,323 B2 | 4/2015 | Miller et al. |
| 9,039,702 B2 | 5/2015 | Miller et al. |
| 9,108,018 B2 | 8/2015 | Dickinson et al. |
| 9,179,916 B2 | 11/2015 | Brenneman et al. |
| 9,192,491 B1 | 11/2015 | Raju et al. |
| 9,259,340 B2 | 2/2016 | Heuser et al. |
| 9,301,830 B2 | 4/2016 | Heuser et al. |
| 9,314,329 B2 | 4/2016 | Dickinson et al. |
| 9,314,556 B2 | 4/2016 | Tuseth |
| 9,326,792 B2 | 5/2016 | Dickinson et al. |
| 9,381,018 B2 | 7/2016 | Cully et al. |
| 9,486,276 B2 | 11/2016 | Rios et al. |
| 9,504,781 B2 | 11/2016 | Kassab et al. |
| 9,522,016 B2 | 12/2016 | Kellerman et al. |
| 9,532,803 B2 | 1/2017 | Dickenson et al. |
| 9,539,124 B1 | 1/2017 | Raju et al. |
| 9,545,263 B2 | 1/2017 | Lenihan et al. |
| 9,649,157 B1 | 5/2017 | Buelna |
| 9,706,998 B2 | 7/2017 | Dickinson et al. |
| 9,724,214 B2 | 8/2017 | Kassab |
| 9,757,542 B2 | 9/2017 | Lupton |
| 9,782,201 B2 | 10/2017 | Dickinson et al. |
| 9,872,693 B2 | 1/2018 | Furuya et al. |
| 9,931,164 B2 | 4/2018 | Kellerman et al. |
| 9,955,970 B2 | 5/2018 | Brenneman et al. |
| 9,955,972 B1 | 5/2018 | Buelna |
| 10,092,427 B2 | 10/2018 | Bonsignore et al. |
| 10,136,987 B2 | 11/2018 | Dickinson et al. |
| 10,159,822 B2 | 12/2018 | Lentz et al. |
| 10,182,902 B2 | 1/2019 | Heuser et al. |
| 10,231,771 B2 | 3/2019 | Kellerman et al. |
| 10,265,206 B2 | 4/2019 | Heuser et al. |
| 10,278,851 B2 | 5/2019 | Reis et al. |
| 10,285,800 B2 | 5/2019 | Dickinson et al. |
| 10,314,591 B2 | 6/2019 | Shields et al. |
| 10,363,354 B2 | 7/2019 | Kassab et al. |
| 10,390,933 B2 | 8/2019 | Dickinson et al. |
| 10,398,580 B2 | 9/2019 | Dickinson et al. |
| 10,405,967 B1 | 9/2019 | Dickinson et al. |
| 10,434,293 B2 | 10/2019 | Park et al. |
| 10,492,936 B2 | 12/2019 | Syed et al. |

(56) References Cited

U.S. PATENT DOCUMENTS

| | | |
|---|---|---|
| 10,517,637 B2 | 12/2019 | Dickinson et al. |
| 10,524,894 B1 | 1/2020 | Dickinson et al. |
| 10,543,308 B2 | 1/2020 | Lenihan et al. |
| 10,596,356 B2 | 3/2020 | Lenihan et al. |
| 10,603,040 B1 | 3/2020 | Berman et al. |
| 10,632,005 B2 | 4/2020 | Gianotti et al. |
| 10,632,293 B2 | 4/2020 | Paris et al. |
| 10,695,065 B1 | 6/2020 | Kellerman et al. |
| 10,695,534 B2 | 6/2020 | Pate |
| 10,736,729 B2 | 8/2020 | Kassab et al. |
| 10,751,461 B2 | 8/2020 | Hull et al. |
| 10,799,259 B2 | 10/2020 | Furuya et al. |
| 10,821,217 B2 | 11/2020 | Pate |
| 10,835,367 B2 | 11/2020 | Dickinson et al. |
| 10,869,717 B2 | 12/2020 | Rios et al. |
| 10,874,422 B2 | 12/2020 | Cohn et al. |
| 10,881,429 B2 | 1/2021 | Dickinson et al. |
| 10,925,710 B2 | 2/2021 | Hall et al. |
| 10,926,068 B2 | 2/2021 | Narayan et al. |
| 10,987,106 B2 | 4/2021 | Paris et al. |
| 11,007,075 B2 | 5/2021 | Bagaoisan et al. |
| 11,026,743 B2 | 6/2021 | Pate et al. |
| 11,051,880 B2 | 7/2021 | Miller et al. |
| 11,090,177 B2 | 8/2021 | Reis et al. |
| 11,116,943 B2 | 9/2021 | Deaton et al. |
| 11,129,965 B2 | 9/2021 | Humbert et al. |
| 11,241,304 B2 | 2/2022 | Dickinson et al. |
| 11,285,028 B2 | 3/2022 | Pate et al. |
| 11,311,700 B2 | 4/2022 | Deaton et al. |
| 2001/0041930 A1 | 11/2001 | Globerman et al. |
| 2002/0048310 A1 | 4/2002 | Heuser |
| 2002/0052644 A1 | 5/2002 | Shaolian et al. |
| 2002/0068869 A1 | 6/2002 | Brisken et al. |
| 2002/0089262 A1 | 7/2002 | Topa et al. |
| 2002/0161383 A1 | 10/2002 | Akin et al. |
| 2002/0173784 A1 | 11/2002 | Sliwa, Jr. et al. |
| 2003/0092667 A1 | 5/2003 | Tachibana et al. |
| 2003/0100916 A1 | 5/2003 | Lee et al. |
| 2003/0109827 A1 | 6/2003 | Lavi et al. |
| 2003/0125799 A1 | 7/2003 | Limon |
| 2003/0139802 A1 | 7/2003 | Wulfman et al. |
| 2003/0153969 A1 | 8/2003 | Dehdashtian et al. |
| 2004/0064081 A1 | 4/2004 | Stanish |
| 2004/0073282 A1 | 4/2004 | Stanish |
| 2004/0097990 A1 | 5/2004 | Zhao |
| 2004/0122508 A1 | 6/2004 | White et al. |
| 2004/0133225 A1 | 7/2004 | Makower |
| 2004/0148005 A1 | 7/2004 | Heuser |
| 2004/0158143 A1 | 8/2004 | Flaherty et al. |
| 2004/0199177 A1 | 10/2004 | Kim |
| 2004/0199243 A1 | 10/2004 | Yodfat |
| 2004/0215220 A1 | 10/2004 | Dolan et al. |
| 2004/0230289 A1 | 11/2004 | DiMatteo et al. |
| 2004/0249335 A1 | 12/2004 | Faul et al. |
| 2005/0004648 A1 | 1/2005 | Boekstegers |
| 2005/0021124 A1 | 1/2005 | Cunniffe et al. |
| 2005/0038501 A1 | 2/2005 | Moore, Jr. et al. |
| 2005/0113798 A1 | 5/2005 | Slater et al. |
| 2005/0165469 A1 | 7/2005 | Hogendijk |
| 2005/0192606 A1 | 9/2005 | Paul, Jr. |
| 2005/0203549 A1 | 9/2005 | Realyvasquez |
| 2005/0209617 A1 | 9/2005 | Koven et al. |
| 2005/0234288 A1 | 10/2005 | Aboul-Hosn et al. |
| 2006/0111770 A1 | 5/2006 | Pavcnik et al. |
| 2006/0116625 A1 | 6/2006 | Renati et al. |
| 2006/0116713 A1 | 6/2006 | Sepetka et al. |
| 2006/0122554 A1 | 6/2006 | Wilk |
| 2006/0173475 A1 | 8/2006 | LaFontaine et al. |
| 2006/0195172 A1 | 8/2006 | Luo et al. |
| 2006/0287709 A1 | 12/2006 | Rao |
| 2007/0051681 A1 | 3/2007 | Nardo et al. |
| 2007/0055344 A1 | 3/2007 | Gittings et al. |
| 2007/0106147 A1 | 5/2007 | Altmann et al. |
| 2007/0123811 A1 | 5/2007 | Squitieri |
| 2007/0179590 A1 | 8/2007 | Lu et al. |
| 2007/0185513 A1 | 8/2007 | Woolfson et al. |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0213808 A1 | 9/2007 | Roubin et al. |
| 2007/0265563 A1 | 11/2007 | Heuser |
| 2007/0270902 A1 | 11/2007 | Slazas et al. |
| 2007/0276468 A1 | 11/2007 | Holzer et al. |
| 2008/0009936 A1 | 1/2008 | Kim et al. |
| 2008/0154153 A1 | 6/2008 | Heuser |
| 2008/0161901 A1 | 7/2008 | Heuser et al. |
| 2008/0161904 A1 | 7/2008 | Heuser et al. |
| 2008/0177249 A1 | 7/2008 | Heuser et al. |
| 2008/0194939 A1 | 8/2008 | Dickinson et al. |
| 2008/0228209 A1 | 9/2008 | Demello et al. |
| 2008/0234813 A1 | 9/2008 | Heuser |
| 2008/0255595 A1 | 10/2008 | Buchbinder et al. |
| 2009/0012429 A1 | 1/2009 | Heuser |
| 2009/0093791 A1 | 4/2009 | Heuser |
| 2009/0182360 A1 | 7/2009 | Makower |
| 2009/0192485 A1 | 7/2009 | Heuser |
| 2009/0292199 A1 | 11/2009 | Bielewicz et al. |
| 2009/0312617 A1 | 12/2009 | Creed et al. |
| 2010/0016709 A1 | 1/2010 | Gilboa et al. |
| 2010/0069820 A1 | 3/2010 | Zotz |
| 2010/0082058 A1 | 4/2010 | Kassab |
| 2010/0087732 A1 | 4/2010 | Eberle et al. |
| 2010/0094391 A1 | 4/2010 | Heraty et al. |
| 2010/0113919 A1 | 5/2010 | Maschke |
| 2010/0131000 A1 | 5/2010 | Demello et al. |
| 2010/0174357 A1 | 7/2010 | LeMaitre et al. |
| 2010/0198056 A1 | 8/2010 | Febro et al. |
| 2010/0241214 A1 | 9/2010 | Holzer et al. |
| 2011/0009740 A1 | 1/2011 | Hauck |
| 2011/0046720 A1 | 2/2011 | Shalev et al. |
| 2011/0054589 A1 | 3/2011 | Bashiri et al. |
| 2011/0077680 A1 | 3/2011 | Heuser |
| 2011/0082490 A1 | 4/2011 | Connelly et al. |
| 2011/0152994 A1 | 6/2011 | Hendriksen et al. |
| 2011/0160751 A1 | 6/2011 | Granja Filho |
| 2011/0197900 A1 | 8/2011 | Heuser |
| 2011/0208109 A1 | 8/2011 | Kassab |
| 2011/0251482 A1 | 10/2011 | Kellerman et al. |
| 2011/0251671 A1 | 10/2011 | Heraty et al. |
| 2011/0264104 A1 | 10/2011 | Naoum |
| 2011/0319902 A1 | 12/2011 | Epstein |
| 2012/0010556 A1 | 1/2012 | Faul et al. |
| 2012/0046678 A1 | 2/2012 | Lemaitre et al. |
| 2012/0046730 A1 | 2/2012 | von Oepen et al. |
| 2012/0065652 A1 | 3/2012 | Cully et al. |
| 2012/0095500 A1 | 4/2012 | Heuser |
| 2012/0116354 A1 | 5/2012 | Heuser |
| 2012/0123512 A1 | 5/2012 | Asfora et al. |
| 2012/0150092 A1 | 6/2012 | McAllister et al. |
| 2012/0179238 A1 | 7/2012 | Sarac et al. |
| 2012/0203329 A1 | 8/2012 | Heuser |
| 2012/0239137 A1 | 9/2012 | Heuser et al. |
| 2012/0271396 A1 | 10/2012 | Zheng et al. |
| 2012/0271400 A1 | 10/2012 | Lyons et al. |
| 2012/0277774 A1 | 11/2012 | Guo |
| 2012/0296368 A1 | 11/2012 | Kassab et al. |
| 2012/0296406 A1 | 11/2012 | Minion |
| 2012/0310319 A1 | 12/2012 | Tieu et al. |
| 2013/0023813 A1 | 1/2013 | Roorda |
| 2013/0030461 A1 | 1/2013 | Marks et al. |
| 2013/0041305 A1 | 2/2013 | Tarlian, Jr. et al. |
| 2013/0041306 A1 | 2/2013 | Faul et al. |
| 2013/0053732 A1 | 2/2013 | Heuser |
| 2013/0060323 A1 | 3/2013 | McHugo |
| 2013/0079697 A1 | 3/2013 | Kaye |
| 2013/0103137 A1 | 4/2013 | Asano et al. |
| 2013/0116500 A1 | 5/2013 | Kohl et al. |
| 2013/0116715 A1 | 5/2013 | Weber |
| 2013/0138139 A1 | 5/2013 | Stanley |
| 2013/0144373 A1 | 6/2013 | Shahriari |
| 2013/0190676 A1 | 7/2013 | Dickinson et al. |
| 2013/0197621 A1 | 8/2013 | Ryan et al. |
| 2013/0204176 A1 | 8/2013 | Duffy et al. |
| 2013/0226067 A1 | 8/2013 | Ward et al. |

(56) References Cited

U.S. PATENT DOCUMENTS

| | | |
|---|---|---|
| 2013/0226285 A1 | 8/2013 | Strommer |
| 2013/0261531 A1 | 10/2013 | Gallagher et al. |
| 2013/0324901 A1 | 12/2013 | Pillai |
| 2013/0331762 A1 | 12/2013 | Kassab et al. |
| 2014/0039538 A1 | 2/2014 | Kassab et al. |
| 2014/0052170 A1 | 2/2014 | Heuser et al. |
| 2014/0088623 A1 | 3/2014 | Yevzlin et al. |
| 2014/0088681 A1 | 3/2014 | Iyer et al. |
| 2014/0088685 A1 | 3/2014 | Yevzlin et al. |
| 2014/0100508 A1 | 4/2014 | Khan |
| 2014/0100510 A1 | 4/2014 | Yevzlin et al. |
| 2014/0142677 A1 | 5/2014 | Heuser et al. |
| 2014/0142679 A1 | 5/2014 | Motaganahalli |
| 2014/0148751 A1 | 5/2014 | Kassab et al. |
| 2014/0194910 A1 | 7/2014 | Orion et al. |
| 2014/0270067 A1 | 9/2014 | Clark |
| 2014/0276335 A1 | 9/2014 | Pate |
| 2014/0324155 A1 | 10/2014 | Paul |
| 2014/0330194 A1 | 11/2014 | Roorda |
| 2014/0336746 A1 | 11/2014 | Woerne |
| 2014/0343582 A1 | 11/2014 | Asfora et al. |
| 2014/0350593 A1 | 11/2014 | Laroya et al. |
| 2014/0358064 A1 | 12/2014 | Dorn |
| 2014/0358221 A1 | 12/2014 | Ho et al. |
| 2014/0364882 A1 | 12/2014 | Tulleken et al. |
| 2014/0371653 A1 | 12/2014 | Criado et al. |
| 2015/0005872 A1 | 1/2015 | Theobald et al. |
| 2015/0011925 A1 | 1/2015 | Buckman, Jr. et al. |
| 2015/0025616 A1 | 1/2015 | Chang |
| 2015/0032095 A1 | 1/2015 | Heuser |
| 2015/0045728 A1 | 2/2015 | Heuser |
| 2015/0173782 A1 | 6/2015 | Garrison et al. |
| 2015/0174379 A1 | 6/2015 | Bagaosian et al. |
| 2015/0209526 A1 | 7/2015 | Matsubara et al. |
| 2015/0223817 A1 | 8/2015 | Paris et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2016/0058956 A1 | 3/2016 | Cohn et al. |
| 2016/0066933 A1 | 3/2016 | Root et al. |
| 2016/0096008 A1 | 4/2016 | Park et al. |
| 2016/0100855 A1 | 4/2016 | Lemaitre et al. |
| 2016/0128855 A1 | 5/2016 | Heuser et al. |
| 2016/0151066 A1 | 6/2016 | Paris et al. |
| 2016/0166754 A1 | 6/2016 | Kassab et al. |
| 2016/0175087 A1 | 6/2016 | Heuser et al. |
| 2016/0175569 A1 | 6/2016 | Heuser |
| 2016/0199626 A1 | 7/2016 | Paris et al. |
| 2016/0213462 A1 | 7/2016 | Szabolcs et al. |
| 2017/0071721 A1 | 3/2017 | Kassab et al. |
| 2017/0119464 A1 | 5/2017 | Rios et al. |
| 2017/0128704 A1 | 5/2017 | Lenihan et al. |
| 2017/0202603 A1 | 7/2017 | Cohn et al. |
| 2017/0202616 A1 | 7/2017 | Pate et al. |
| 2017/0216032 A1 | 8/2017 | Van Bladel et al. |
| 2017/0239035 A1 | 8/2017 | Schreck et al. |
| 2017/0354416 A1 | 12/2017 | Dickenson et al. |
| 2018/0000512 A1 | 1/2018 | Dickinson et al. |
| 2018/0071120 A1 | 3/2018 | Sullivan |
| 2018/0098869 A1 | 4/2018 | Reis et al. |
| 2018/0116522 A1 | 5/2018 | Brenneman et al. |
| 2018/0185563 A1 | 7/2018 | Pillai |
| 2018/0243115 A1 | 8/2018 | Ehnes et al. |
| 2018/0271637 A1 | 9/2018 | Hall et al. |
| 2018/0271638 A1 | 9/2018 | Hall et al. |
| 2018/0333283 A1 | 11/2018 | Fleming |
| 2018/0344396 A1 | 12/2018 | Miller et al. |
| 2019/0083228 A1 | 3/2019 | Dickinson et al. |
| 2019/0083717 A1 | 3/2019 | Matsubara et al. |
| 2019/0126017 A1 | 5/2019 | Hall et al. |
| 2019/0133678 A1 | 5/2019 | Pate et al. |
| 2019/0134349 A1 | 5/2019 | Cohn et al. |
| 2019/0246631 A1 | 8/2019 | Tillman et al. |
| 2019/0254846 A1 | 8/2019 | Gianotti et al. |
| 2019/0262118 A1 | 8/2019 | Eigler et al. |
| 2019/0269888 A1 | 9/2019 | Chao et al. |
| 2019/0274855 A1 | 9/2019 | Pate et al. |
| 2019/0275293 A1 | 9/2019 | Lenihan et al. |
| 2019/0290828 A1 | 9/2019 | Deur |
| 2019/0298909 A1 | 10/2019 | Cully et al. |
| 2019/0321606 A1 | 10/2019 | Lenihan et al. |
| 2019/0358020 A1 | 11/2019 | Dickinson et al. |
| 2019/0366062 A1 | 12/2019 | Park et al. |
| 2020/0022829 A1 | 1/2020 | Reis et al. |
| 2020/0061338 A1 | 2/2020 | Pate |
| 2020/0086094 A1 | 3/2020 | Paris et al. |
| 2020/0161144 A1 | 5/2020 | Lenihan et al. |
| 2020/0171282 A1 | 6/2020 | Sullivan |
| 2020/0187879 A1 | 6/2020 | Purcell |
| 2020/0214827 A1 | 7/2020 | Dickinson et al. |
| 2020/0246531 A1 | 8/2020 | Lenihan et al. |
| 2020/0289149 A1 | 9/2020 | Cohn et al. |
| 2020/0305951 A1 | 10/2020 | Reu et al. |
| 2020/0353153 A1 | 11/2020 | Hull et al. |
| 2020/0368047 A1 | 11/2020 | Kum |
| 2021/0128228 A1 | 5/2021 | Rios et al. |
| 2021/0166950 A9 | 6/2021 | Lenihan et al. |
| 2021/0177420 A1 | 6/2021 | Paris et al. |
| 2021/0220616 A1 | 7/2021 | Deaton et al. |
| 2021/0220623 A1 | 7/2021 | Humbert et al. |
| 2021/0244434 A1 | 8/2021 | Popa et al. |
| 2021/0267675 A1 | 9/2021 | Pate et al. |
| 2021/0322189 A1 | 10/2021 | Schwartz et al. |
| 2021/0338412 A1 | 11/2021 | MacTaggart et al. |
| 2021/0361317 A1 | 11/2021 | Dickinson et al. |
| 2021/0369343 A1 | 12/2021 | Miller et al. |
| 2021/0369344 A1 | 12/2021 | Miller et al. |
| 2022/0008693 A1 | 1/2022 | Humbert et al. |
| 2022/0125572 A1 | 4/2022 | Dickinson et al. |

FOREIGN PATENT DOCUMENTS

| | | |
|---|---|---|
| CN | 1204244 | 1/1999 |
| CN | 1460029 | 12/2003 |
| CN | 2728440 Y | 9/2005 |
| CN | 2843384 Y | 12/2006 |
| EP | 0 467 516 A1 | 1/1992 |
| EP | 0 248 761 B1 | 4/1992 |
| EP | 1 307 163 | 5/2003 |
| EP | 0 910 298 B1 | 8/2003 |
| EP | 0 994 682 B1 | 12/2003 |
| EP | 0 888 094 B1 | 2/2004 |
| EP | 1 066 804 B1 | 7/2004 |
| EP | 1 229 863 B1 | 9/2004 |
| EP | 0 951 251 B1 | 3/2005 |
| EP | 0 973 577 B1 | 3/2005 |
| EP | 1 126 796 B1 | 6/2005 |
| EP | 1 059 894 B1 | 7/2005 |
| EP | 0 949 889 B1 | 9/2005 |
| EP | 1 067 869 B1 | 11/2005 |
| EP | 1 129 673 B1 | 11/2005 |
| EP | 1 295 575 B1 | 1/2006 |
| EP | 1 613 373 | 1/2006 |
| EP | 1 295 573 B1 | 2/2006 |
| EP | 1 051 129 B1 | 4/2006 |
| EP | 1 112 043 B1 | 4/2006 |
| EP | 0 909 198 B1 | 6/2006 |
| EP | 1 295 572 B1 | 7/2006 |
| EP | 0 888 093 B2 | 12/2006 |
| EP | 1 119 387 B1 | 2/2007 |
| EP | 0 964 636 B1 | 8/2007 |
| EP | 1 359 967 B1 | 8/2007 |
| EP | 1 187 559 B1 | 9/2007 |
| EP | 1 299 145 B1 | 9/2007 |
| EP | 1 377 335 B1 | 10/2007 |
| EP | 1 112 042 B1 | 11/2007 |
| EP | 1 477 133 B9 | 11/2007 |
| EP | 1 295 574 B1 | 4/2008 |
| EP | 1 117 458 | 2/2009 |
| EP | 1 286 628 B1 | 3/2009 |
| EP | 1 253 859 B1 | 4/2009 |
| EP | 1 600 110 B1 | 4/2009 |
| EP | 1 653 885 B1 | 4/2009 |
| EP | 0 955 933 B1 | 8/2009 |

(56) References Cited

FOREIGN PATENT DOCUMENTS

| | | |
|---|---|---|
| EP | 0 893 977 B2 | 10/2009 |
| EP | 1 827 307 B1 | 5/2010 |
| EP | 1 598 031 B1 | 6/2010 |
| EP | 1 790 314 B1 | 6/2010 |
| EP | 1 779 809 B1 | 8/2010 |
| EP | 1 341 482 B1 | 10/2010 |
| EP | 1 047 341 B1 | 12/2010 |
| EP | 1 820 436 B1 | 12/2010 |
| EP | 1 496 956 B1 | 4/2011 |
| EP | 1 815 803 B1 | 5/2011 |
| EP | 1 317 908 B1 | 7/2011 |
| EP | 1 527 751 B1 | 7/2011 |
| EP | 1 658 812 B1 | 10/2011 |
| EP | 1 447 052 B1 | 2/2012 |
| EP | 1 614 400 B1 | 4/2012 |
| EP | 2 582 306 A1 | 4/2013 |
| EP | 2 640 280 | 9/2013 |
| EP | 1 550 479 B1 | 9/2015 |
| EP | 2 613 822 B1 | 11/2017 |
| EP | 3 267 951 | 1/2018 |
| EP | 2 379 130 B1 | 2/2018 |
| EP | 2 841 027 B1 | 8/2018 |
| EP | 2 063 823 | 10/2018 |
| EP | 3 322 470 | 11/2018 |
| EP | 3 322 471 | 11/2018 |
| EP | 3 402 426 | 11/2018 |
| EP | 3 402 432 | 11/2018 |
| EP | 3 402 561 | 11/2018 |
| EP | 2 968 852 | 7/2019 |
| EP | 3 515 322 | 7/2019 |
| EP | 3 302 231 | 8/2019 |
| EP | 2 812 063 B1 | 3/2020 |
| EP | 3 099 372 | 11/2020 |
| EP | 3 064 171 B1 | 1/2021 |
| EP | 3 275 402 B1 | 8/2021 |
| GB | 2536362 | 3/2017 |
| JP | S62-298347 | 12/1987 |
| JP | 2002-516704 | 6/2002 |
| JP | 2004-501720 | 1/2004 |
| JP | 2010-269161 | 12/2010 |
| JP | 2012-040394 | 3/2012 |
| JP | 2013-528112 | 7/2013 |
| WO | WO 1991/001689 | 2/1991 |
| WO | WO 1997/013463 | 4/1997 |
| WO | WO 1997/013471 | 4/1997 |
| WO | WO 2000/009041 | 2/2000 |
| WO | WO 2000/033770 | 6/2000 |
| WO | WO 2000/045886 | 8/2000 |
| WO | WO 2001/49187 | 7/2001 |
| WO | WO 2002/002163 | 1/2002 |
| WO | WO 2004/098684 | 11/2004 |
| WO | WO 2005/065579 | 7/2005 |
| WO | WO 2009/107142 | 9/2009 |
| WO | WO 2009/150099 | 12/2009 |
| WO | WO 2010/107950 A1 | 9/2010 |
| WO | WO 2011/107249 | 9/2011 |
| WO | WO 2011/163322 | 12/2011 |
| WO | WO 2013/033215 | 3/2013 |
| WO | WO 2013/113704 | 8/2013 |
| WO | WO 2014/137830 | 9/2014 |
| WO | WO 2014/145021 | 9/2014 |
| WO | WO 2014/162067 | 10/2014 |
| WO | WO 2014/176458 | 10/2014 |
| WO | WO 2015/017714 | 2/2015 |
| WO | WO 2015/108984 | 7/2015 |
| WO | WO 2015/195668 | 12/2015 |
| WO | WO 2016/145202 | 9/2016 |
| WO | WO 2017/011402 | 1/2017 |
| WO | WO 2018/057095 | 3/2018 |
| WO | WO 2018/164766 | 9/2018 |
| WO | WO 2018/189593 | 10/2018 |
| WO | WO 2019/202339 | 10/2019 |
| WO | WO 2019/236900 | 12/2019 |
| WO | WO 2020/072717 | 4/2020 |
| WO | WO 2020/076833 | 4/2020 |
| WO | WO 2020/242491 | 12/2020 |
| WO | WO 2021/087294 | 5/2021 |
| WO | WO 2021/137851 | 7/2021 |
| WO | WO 2021/221607 | 11/2021 |

OTHER PUBLICATIONS

Alexandrescu et al., "Deep calf veins arterialization for inferior limb preservation in diabetic patients with extended ischaemic wounds, unfit for direct arterial reconstruction: preliminary results according to an angiosome model of perfusion", *Cardiovasc. Revasc. Med.*, Jan.-Feb. 2011, vol. 12, pp. 10-19.

Busato et al., "The great saphenous vein in situ for the arterialization of the venous arch of the foot", *J. Casc. Bras.*, 2010, vol. 9, No. 3, pp. 119-123.

Djoric et al., "Distal Venous Arterialization and Reperfusion Injury: Focus on Oxidative Status", *Eur. Surg. Res.*, 2012, vol. 48, pp. 200-207.

Djoric, "Early individual experience with distal venous arterialization as a lower limb salvage procedure", *Am. Surg.*, Jun. 2011, vol. 77, No. 6, pp. 726-730 (Abstract Only).

Engelke et al., "Distal Venous Arterialization for Lower Limb Salvage: Angiographic Appearances and Interventional Procedures", *Radiographics*, Sep.-Oct. 2001, vol. 21, No. 5, pp. 1239-1248.

Gasparis et al., "Distal venous arterialization for limb salvage—a case report", *Vasc. Endovascular Surg.*, Nov.-Dec. 2002, vol. 36, No. 6, pp. 469-472 (Abstract Only).

Gavrilenko et al., "Long-term results of venous blood flow arterialization of the leg and foot in patients with critical lower limb ischemia", *Angiol. Sosud. Khir.*, 2007, vol. 13, No. 2, pp. 95-103 (Abstract Only).

Houlind et al., "Early results from an angiosome-directed open surgical technique for venous arterialization in patients with critical limb ischemia", *Diabet. Foot Ankle*, Dec. 2013, vol. 17, No. 4.

Jacob et al., "Vascular surgical society of great britain and ireland: distal venous arterialization for non-reconstructable arterial disease", *Br. J. Surg.*, May 1999, vol. 86, No. 5, p. 694 (Abstract Only).

Kassab et al., "Coronary venous retroperfusion: an old concept, a new approach", *J. Appl. Physiol.*, Feb. 2008, vol. 104, pp. 1266-1272.

Keshelava et al., "Foot venous system arterialization for salvage of nonreconstructable acute ischemic limb: a case report", *J. Vasc. Nurs.*, Mar. 2009, vol. 27, No. 1, pp. 13-16 (Abstract Only).

Kopelman et al., "Prevention of limb loss in critical ischaemia by arterialization of the superficial venous system: an experimental study in dogs", *Cardiovasc. Surg.*, Aug. 1998, vol. 6, No. 4, pp. 384-388 (Abstract Only).

Lengua et al., "Arterialization of the distal veins of the foot for limb salvage in arteritis—Techniques and results", *Ann. Chir.*, Sep. 2001, vol. 126, No. 7, pp. 629-638 (Abstract Only).

Lu et al., "Meta-analysis of the Clinical Effectiveness of Venous Arterialization for Salvage of Critically Ischaemic Limbs", *Eur. J. Vasc. Endovasc. Surg.*, May 2006, vol. 31, pp. 493-499.

Matarrese et al., "Revascularization of the ischemic hand with arterialization of the venous system", *J. Hand. Surg. Am.*, Dec. 2011, vol. 36, No. 12, pp. 2047-2051 (Abstract Only).

Miasnik et al., "Scintigraphic evaluation of the efficacy of nonstandard methods of treating critical ischemia of the lower limbs", *Khirurgiia (Mosk)*, 2002, vol. 6, pp. 48-51 (Abstract Only).

Mutirangura et al., "Pedal bypass with deep venous arterialization: the therapeutic option in critical limb ischemia and unreconstructable distal arteries", *Vascular*, Dec. 2011, vol. 19, No. 6, pp. 313-319.

Nguyen et al., "Treatment of hand ischemia with arterialization of the venous system of the hand: report of three cases", *Ann. Chir. Plast. Esthet.*, Jun. 2011, vol. 56, No. 3, pp. 200-206 (Abstract Only).

Pederson, "Revascularization of the chronically ischemic hand", *Hand Clin*, Nov. 1999, vol. 15, No. 4, pp. 629-642 (Abstract Only).

(56) References Cited

OTHER PUBLICATIONS

Pokrovsky et al., "Arterialization of the hand venous system in patients with critical ischemia and thromboangiitis obliterans", *Angiol. Sosud. Khir.*, 2007, vol. 13, No. 2, pp. 105-111 (Abstract Only).
Rowe et al., "Initial experience with dorsal venous arch arterialization for limb salvage", *Ann. Vasc. Surg.*, Feb.-Mar. 2002, vol. 16, No. 2, pp. 187-192 (Abstract Only).
Sangiorgi et al, "The Cutaneous Microvascular Architecture of Human Diabetic Toe Studied by Corrosion Casting and Scanning Electron Microscopy Analysis", *Anat. Rec.*, Oct. 2010, vol. 293, pp. 1639-1645.
Sasajima et al., "Combined distal venous arterialization and free flap for patients with extensive tissue loss", *Ann. Vasc. Surg.*, Apr. 2010, vol. 24, No. 3, pp. 373-381 (Abstract Only).
Schreve et al., "Comparative study of venous arterialization and pedal bypass in a patient cohort with critical limb ischemia", *Ann. Vasc. Surg.*, Jul. 2014; vol. 28, No. 5, pp. 1123-1127 (Abstract Only).
Sheil, "Treatment of critical ischaemia of the lower limb by venous arterialization : an interim report", *Br. J. Surg.*, Mar. 1977, vol. 64, No. 3, pp. 197-199 (Abstract Only).
U.S. Appl. No. 16/532,809, Method for Fluid Flow Through Body Passages, filed Aug. 6, 2019.
U.S. Appl. No. 16/552,241 (U.S. Pat. No. 10,524,894), Methods for Effecting Retroperfusion in a Body Passage, filed Aug. 27, 2019 (Jan. 7, 2020).
Augsburger et al., "Effect of Flow Diverter Porosity on Intraaneurysmal Blood Flow", *Clinical Neuroradiology*, 2009, No. 3, pp. 204-214.
U.S. Appl. No. 17/225,365, Methods for Accessing Pedal Veins, filed Apr. 8, 2021.
U.S. Appl. No. 17/225,380, Devices and Methods for Catheter Alignment, filed Apr. 8, 2021.
U.S. Appl. No. 17/361,752, Methods for Accessing Pedal Veins, filed Jun. 29, 2021.
U.S. Appl. No. 16/191,769, Devices for Fluid Flow Through Body Passages, filed Nov. 15, 2018.
U.S. Appl. No. 16/532,809, Apparatus and Method for Fluid Flow Through Body Passages, filed Aug. 6, 2019.
U.S. Appl. No. 11/662,128, Minimally Invasive Surgical Apparatus and Methods, filed Sep. 8, 2005.
U.S. Appl. No. 14/141,913 (U.S. Pat. No. 10,398,580), Minimally Invasive Surgical Apparatus and Methods, filed Dec. 27, 2013 (Sep. 3, 2019).
U.S. Appl. No. 12/297,498 (U.S. Pat. No. 8,439,963), Apparatus and Method for Maintaining Fluid Flow Through Body Passages, filed Apr. 20, 2007 (May 14, 2013).
U.S. Appl. No. 13/791,185, Devices for Fluid Flow Through Body Passages, filed Apr. 8, 2014.
U.S. Appl. No. 14/592,128 (U.S. Pat. No. 9,532,803), Methods for Fluid Flow Through Body Passages, filed Jan. 8, 2015 (Jan. 3, 2017).
U.S. Appl. No. 14/718,477 (U.S. Pat. No. 9,326,792), Methods for Fluid Flow Through Body Passages, filed May 21, 2015 (May 3, 2016).
U.S. Appl. No. 14/592,163 (U.S. Pat. No. 9,108,018), Methods for Fluid Flow Through Body Passages, filed Jan. 8, 2015 (Aug. 18, 2015).
U.S. Appl. No. 15/143,864 (U.S. Pat. No. 9,782,201), Methods for Fluid Flow Through Body Passages, filed May 2, 2016 (Oct. 10, 2017).
U.S. Appl. No. 15/390,925 (U.S. Pat. No. 10,136,987), Devices for Fluid Flow Through Body Passages, filed Dec. 27, 2016 (Nov. 27, 2018).
U.S. Appl. No. 15/701,060 (U.S. Pat. No. 10,390,933), Devices for Fluid Flow Through Body Vessels, filed Sep. 11, 2017 (Aug. 27, 2019).
U.S. Appl. No. 16/191,769 (U.S. Pat. No. 10,835,367), Devices for Fluid Flow Through Body Passages, filed Nov. 15, 2018 (Nov. 17, 2020).
U.S. Appl. No. 16/532,809 (U.S. Pat. No. 11,241,304), Method for Fluid Flow Through Body Passages, filed Aug. 6, 2019 (Feb. 8, 2022).
U.S. Appl. No. 17/573,028, Apparatus and Method for Fluid Flow Through Body Passages, filed Jan. 11, 2022.
U.S. Appl. No. 14/834,813 (U.S. Pat. No. 9,314,329), Methods and Systems for Providing or Maintaining Fluid Flow Through Body Passages, filed Aug. 25, 2015 (Apr. 19, 2016).
U.S. Appl. No. 15/084,999 (U.S. Pat. No. 9,706,998), Methods for Targeting Body Passages, filed Mar. 30, 2016 (Jul. 18, 2017).
U.S. Appl. No. 15/648,695 (U.S. Pat. No. 10,285,800), Systems for Providing or Maintaining Fluid Flow Through Body Passages, filed Jul. 13, 2017 (May 14, 2019).
U.S. Appl. No. 16/410,932 (U.S. Pat. No. 10,405,967), Methods for Puncturing an Expandable Member to Confirm Advancement Into a Body Passage, filed May 13, 2019 (Sep. 10, 2019).
U.S. Appl. No. 16/552,241 (U.S. Pat. No. 10,524,894), Methods for Targeting a Body Passage to Effect Fluid Flow, filed Aug. 27, 2019 (Jan. 7, 2020).
U.S. Appl. No. 16/717,164, Methods for Targeting a Body Passage to Effect Fluid Flow, filed Dec. 17, 2019.
U.S. Appl. No. 14/718,427 (U.S. Pat. No. 9,545,263), Devices and Methods for Treating Lower Extremity Vasculature, filed May 21, 2015 (Jan. 17, 2017).
U.S. Appl. No. 15/405,707, Devices and Methods for Treating Lower Extremity Vasculature, filed Jan. 13, 2017.
U.S. Appl. No. 16/426,280 (U.S. Pat. No. 10,596,356), Methods for Placing a Stent-Graft to Cover Collateral Vessels in Lower Extremity Vasculature, filed May 30, 2019 (Mar. 24, 2020).
U.S. Appl. No. 16/426,375 (U.S. Pat. No. 10,543,308), Methods for Routing a Guidewire From a First Vessel and Through a Second Vessel in Lower Extremity Vasculature, filed May 30, 2019 (Jan. 28, 2020).
U.S. Appl. No. 16/747,825, Methods for Routing a Guidewire From a First Vessel and Through a Second Vessel in Lower Extremity Vasculature, filed Jan. 21, 2020.
U.S. Appl. No. 17/225,365 (U.S. Pat. No. 11,116,943), Methods for Accessing Pedal Veins, filed Apr. 8, 2021 (Sep. 14, 2021).
U.S. Appl. No. 17/225,380 (U.S. Pat. No. 11,129,965), Devices and Methods for Catheter Alignment, filed Apr. 8, 2021 (Sep. 28, 2021).
U.S. Appl. No. 17/482,803, Devices and Methods for Catheter Alignment, filed Sep. 23, 2021.
U.S. Appl. No. 17/361,752 (U.S. Pat. No. 11,311,700), Methods for Accessing Pedal Veins, filed Jun. 29, 2021 (Apr. 26, 2022).
U.S. Appl. No. 17/592,172, Methods for Accessing Pedal Veins for Deep Vein Arterialization, filed Feb. 3, 2022.
U.S. Appl. No. 17/731,588, Devices and Methods for Diverting Blood Flow From a First Vessel, filed Apr. 28, 2022.
U.S. Appl. No. 17/731,664, Devices and Methods for Increasing Blood Perfusion to a Distal Extremity, filed Apr. 28, 2022.

MINIMALLY INVASIVE SURGICAL APPARATUS AND METHODS

FIELD OF THE INVENTION

The invention relates to apparatus and methods for performing percutaneous catheter-based interventional surgery. In particular, the invention relates to apparatus and techniques for transvascular interstitial surgery.

BACKGROUND

Minimally invasive surgery, or 'key-hole' surgery, allows for surgical devices to be inserted into a patient's body cavity through a small aperture cut. This form of surgery has become increasingly popular as it allows patients treated successfully to suffer less surgical discomfort while retaining the benefits of conventional surgery. Patients treated by such techniques are exposed to lower levels of trauma and their recovery times can be significantly reduced compared to conventional surgical procedures.

Key-hole surgery has been adopted as a favoured route for performing laparoscopic surgery as well as in a number of cardiovascular procedures. In the latter case, a balloon catheter may be used to open a partially occluded coronary artery as an alternative to open heart surgery. This technique is known as balloon angioplasty. The balloon catheter is typically a small, hollow, flexible tube that has a balloon near to its distal tip. The catheter is inserted into an artery (usually near the patient's groin) and then guided through the body to the patient's heart. The heart and cardiac arteries are visualized by using X-ray fluoroscopy, and blockages in the heart vessels are identified. A balloon catheter is then inserted in or near the blockage and inflated, thus widening the occluded blood vessel and helping to restore blood flow to the cardiac tissue.

However, balloon angioplasty is not always a suitable measure, especially in acute cases and in cases where a coronary artery is completely occluded. In these instances the typical treatment is to employ coronary bypass which involves open-heart surgery. Hence, there is a need to provide new and improved methods and apparatus for use in minimally invasive surgical procedures, such the restoration of a blood supply to ischaemic tissue.

Conventional coronary bypass surgery is not always an option for certain patients. Factors such as age, obesity, diabetes and smoking can exclude a proportion of candidate patients who are in genuine need of such treatment. In these cases it has been postulated that minimally invasive surgery could provide a means for treating a broader range of patients including those currently excluded from standard techniques. Oesterle et al (Catheterization and Cardiovascular Interventions (2003) 58: 212-218) describe a technique they call percutaneous in situ coronary venous arterialization (PICVA) which is a catheter based coronary bypass procedure. In PICVA, the occlusion in the diseased artery is 'bypassed' by creation of a channel between the coronary artery and the adjacent coronary vein. In this way the arterial blood is diverted into the venous system and can perfuse the cardiac tissue in a retrograde manner (retroperfusion). The technique of retroperfusion has been known for some time, having first been performed in humans by Beck in the 1940s and 1950s (for review see Keelan et al. Current Interventional Cardiology Reports (2000) 2: 11-19). Apparatus and methods for performing procedures like PICVA are described in WO-A-99/49793 and US-A-2004/0133225.

However, as the clinical results show in Oesterle et al. (supra), successfully performing a minimally invasive procedure of diverting blood flow from the coronary artery to the adjacent vein has a low success rate. In six out of the 11 cases described this was simply due to an inability to target the adjacent vein from the artery. As such, Oesterle et al's procedure is too often doomed to failure before it even starts. At present, the means for targeting the catheter consist of a combination of X-ray fluoroscopy and an imaging ultrasound probe located on the distal tip of the catheter (e.g. see US-A-2004/0133225). Indeed, such an arrangement is difficult to navigate and localisation of the adjacent vein requires considerable skill on the part of the clinician. Hence, there is a need for improvements in the means for targeting devices, such as catheters, that are used for procedures such as PICVA and in general transvascular surgery. Indeed, in the absence of such improvement it seems that such techniques will remain peripheral to the conventional surgical procedures of open-heart coronary bypass.

SUMMARY OF THE INVENTION

The present invention provides means, methods and apparatus for overcoming the problems identified in the prior art. Most notably, the means, methods and apparatus of the invention allow for greatly improved targeting and localisation of the therapy to be administered. Hence, the invention shows particular advantage in treating patients requiring coronary bypass by enabling minimally invasive surgical techniques to be used more successfully than previously known.

Accordingly, in a first aspect the invention provides a means for directing therapy within the body of a patient, the means comprising:
  a) a first therapeutic device that is located in a first body cavity, the first therapeutic device comprising signal means for generating a directional signal;
  b) a second therapeutic device located in a second body cavity adjacent to the first body cavity, the second therapeutic device comprising receiving means for receiving the directional signal; and
  c) therapeutic means for administering therapy to the body of the patient
wherein, therapy is directed by aligning the first therapeutic device with the second therapeutic device via the directional signal transmitted by the first therapeutic device being received by the second therapeutic device, and administering therapy at a location that is aligned to the path taken by the directional signal.

Optionally the therapeutic means is comprised within either the first or the second therapeutic devices. Typically, the first and second medical devices are catheters. In embodiments of the invention where the first therapeutic device comprises the therapeutic means, the first device is also referred to herein as the 'launching device'. Likewise, where the second therapeutic device does not comprise the therapeutic means it is, thus, also referred to herein as the 'target device'.

A second aspect of the invention provides means for aligning a first therapeutic device located in a first body cavity with a second therapeutic device located in a second body cavity adjacent to the first body cavity, the means comprising:
  a) signal means for generating a directional signal, the signal means being located in the first therapeutic device; and b) receiving means for receiving the directional signal, the receiving means being located in the second therapeutic device;

wherein, alignment of the first therapeutic device and the second therapeutic device is achieved when the directional signal transmitted by the first therapeutic device is received by the second therapeutic device.

A third aspect of the invention provides apparatus for traversing tissue intervening first and second body cavities comprising:

a) a launching device suitable for location within the first body cavity, the launching device comprising
   (i) an elongate outer sheath with a distal end and a proximal end, the outer sheath defining and enclosing an interior lumen;
   (ii) a signal transducer located at the distal end of the outer sheath, the signal transducer being arranged so as to transmit a directional signal; and
   (iii) traversing means for traversing the tissue intervening the first and second body cavities, the traversing means being located within the lumen at the distal end of the outer sheath, wherein in use the traversing means is in a retracted state and can be extended out of the lumen via an aperture in the outer sheath such that it engages and traverses the tissue intervening the first and second body cavities, and wherein extension of the traversing means is along a path that is aligned with the direction of the signal;
and,
b) a target device suitable for location within the second body cavity, the target device comprising
   (i) an elongate outer sheath with a distal end and a proximal end, the outer sheath defining and enclosing an interior lumen; and
   (ii) a signal receiving transducer located at the distal end of the outer sheath;

wherein, in use, the signal transducer on the launching device transmits the directional signal that is capable of being received by the signal receiving transducer on the target device, and when the signal is received by the signal receiving transducer on target device it is determined that the devices are located in the correct juxtaposition within their respective body cavities such that the traversing means can be extended out of the launching device and traverses the tissue intervening the first and second body cavities.

A fourth aspect of the invention provides a method for directing therapy in the body of a patient, comprising:

a) placing a first therapeutic device into a first body cavity, the first therapeutic device comprising signal means for generating a directional signal, and therapeutic means for administering therapy to the body of the patient; and
b) placing a second therapeutic device into a second body cavity that is adjacent to the first body cavity, the second therapeutic device comprising receiving means for receiving the directional signal;

wherein, therapy is directed by aligning the first therapeutic device with the second therapeutic device via the directional signal transmitted by the first therapeutic device being received by the second therapeutic device, and administering therapy at a location that is aligned to the path taken by the directional signal.

In a particular embodiment of the invention the step of administering therapy comprises creation of an aperture in tissue between the first and second body cavities, thereby allowing fluid communication between the first and second body cavities. In accordance with the invention, the aperture is created at a position that lies along the path taken by the directional signal.

All references cited herein are incorporated by reference in their entirety. Unless otherwise defined, all technical and scientific terms used herein have the same meaning as commonly understood by one of ordinary skill in the art to which this invention belongs.

The invention is further illustrated by reference to the accompanying drawings in which.

DETAILED DESCRIPTION OF THE INVENTION

Figure 1:
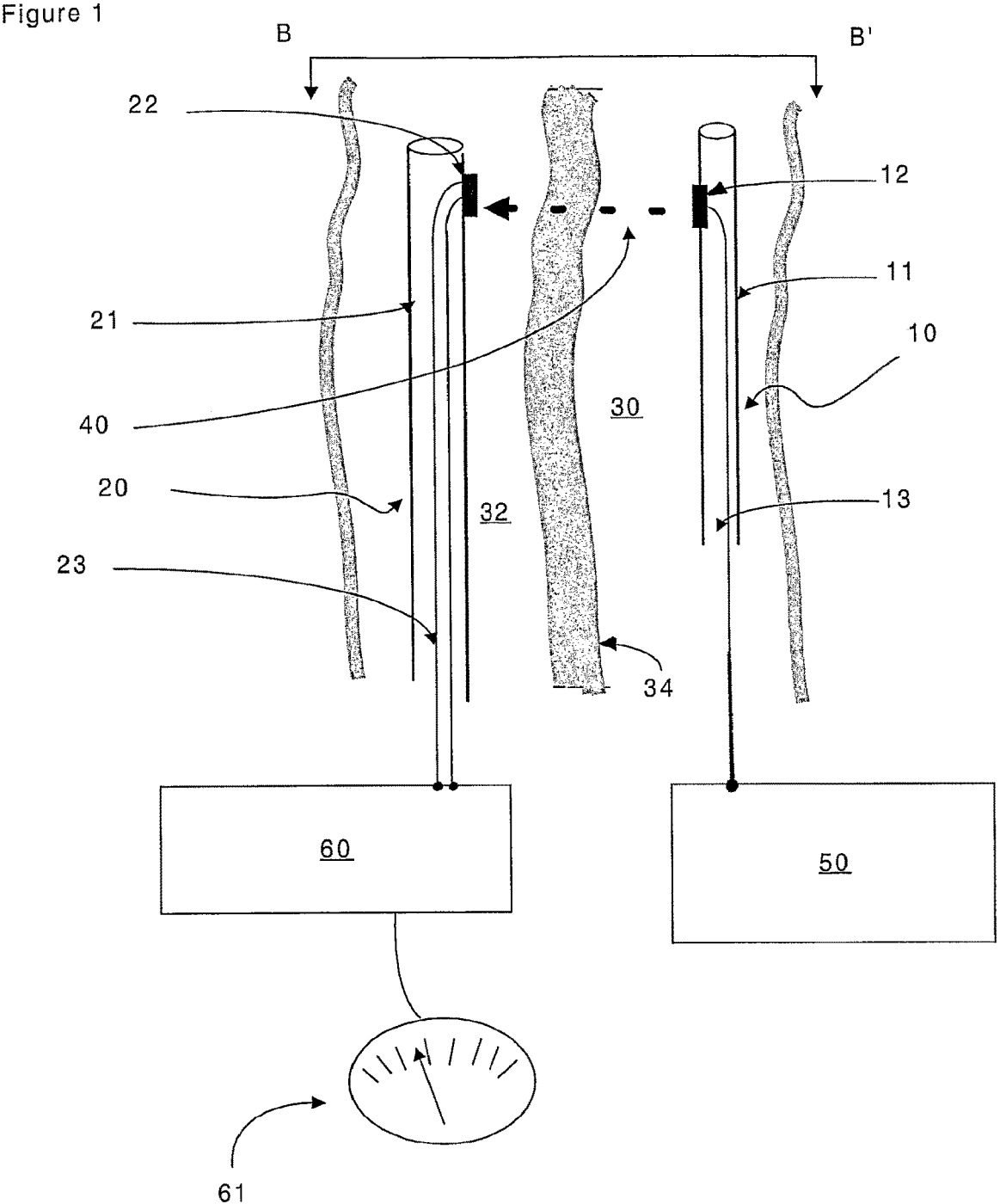
FIG. 1 is a representation of an embodiment of the invention in which the launching device directs a signal from a first body cavity to the target device located in an adjacent second body cavity.

In the embodiment of the invention as shown in FIG. 1, there is provided a launching device (10), which comprises a signal transmitter (12). The launching device (10) is typically a catheter that consists of an elongate flexible rod-like portion and a tip portion, and which provides a conduit for administering therapy within the body of a patient. Hence, the launching device (10) is suitable for location and movement through a first cavity or vessel (30) within a patient's body. The elongate portion of the launching device (10) comprises an outer sheath (11) that encloses a space, defining a lumen (13). The space within the lumen (13) may be suitably partitioned or subdivided as necessary so as to define channels for administering therapy or controlling the positioning of the launching device (10). Such subdivision may, for instance, be achieved either longitudinally or concentrically in an axial fashion.

A signal transducer (12) is located on the launching device (10). The signal transducer (12) provides a signal (40) that is directed outwards from the first launching device (10). In the embodiment shown in FIG. 1 the signal (40) is directed radially outward from the launching device (10) in a direction that is perpendicular to the longitudinal axis of the launching device (10). As mentioned in greater detail below, in alternative embodiments of the invention the direction of the signal (40) need not be perpendicular and can be directed at an angle to that of the axis of the launching device (10). The signal transducer (12) is, thus, comprised within the signal generating means of the apparatus of the invention.

The signal transducer (12) is connected to signal transmitter (50). The signal transmitted can be suitably selected from ultrasound or appropriate electromagnetic sources such as a laser, microwave radiation or via radio waves. In a specific embodiment of the invention described in further detail below, the signal transmitter (50) generates an ultrasound signal, which is relayed to the signal transducer (12), which in turn directs the signal (40) out of the body cavity (30) into the surrounding tissue.

According to the invention, a second device is located within an adjacent second body cavity or vessel (32). The first and second body cavities (30 and 32 respectively) are separated by intervening tissue (34), sometimes referred to as interstitial tissue or a septum. The first and second body cavities (30, 32) are located next to each other in a parallel fashion for at least a portion of their respective lengths. For example, many of the veins and arteries of the body are known to run in parallel with each other for at least a portion of their overall length.

The second device is the target device (20), which assumes a similar arrangement to that of the first device (10). The target device (20) can also be a catheter that consists of an elongate flexible rod-like portion and a tip portion, such that fine movement and positioning of the target device (20) within the body cavity (32) can be achieved. In common with the launching device (10) the target device (20) comprises an outer sheath (21) that encloses a space, defining a lumen (23). The lumen (23) can be suitably partitioned as with the launching device (10).

The target device (20) comprises a receiving transducer (22) for receiving the signal (40). The receiving transducer (22) is comprised within the signal detection means of the apparatus of the invention. In use, when the receiving transducer (22) receives the signal (40) transmitted from signal transducer (12), it transmits the received signal to signal detector (60). The signal detector (60) provides an output reading to the user of the apparatus via output display (61).

In this way, the transmission and detection of the directed signal (40) allows for the navigation and positioning of the launching device (10) relative to the target device (20). In use, the launching device (10) and target device (20) can be manoeuvred by the user of the apparatus until the output display (61) indicates that signal (40) is being received by the target device (40).

In a specific embodiment of the invention, the signal (40) is an ultrasound signal. The signal (40) is directional and is emitted by the signal transducer (12) in shape of a narrow cone or arc—i.e. with the width of the signal band increasing as the distance from the signal transducer (12) increases. Hence, the precision of alignment between the launching device (10) and the target device (20) depends not only upon signal detection but also upon the distance between the two devices, as at greater distances the signal bandwidth is also greater. This level of error is referred to as 'positional uncertainty'. It will be appreciated that a certain level of tolerance exists for positional uncertainty, however, if therapy is to be directed with precision the amount of uncertainty should be minimised. For example, if the diameter (d) of the signal transducer (12) is 1 mm and the frequency of the ultrasound signal is 30 MHz, then the positional uncertainty (x)—i.e. the margin of error on either side of a centre line—will be 1 mm at a perpendicular separation of 5 mm between the launching and target devices (10, 20). For clinical applications of the invention, it is preferred that the positional uncertainty does not exceed around +/−5 mm (that is a total signal bandwidth of 10 mm at the point reception). More preferably, the positional uncertainty should be between around +/−0.01 mm and around +/−4.50 mm. Even more preferably, the positional uncertainty should be between around +/−0.1 mm and around +/−2 mm. Ideally, the positional uncertainty does not exceed around +/−1 mm.

The strength of the signal (40) will also be a determining factor and it will be appreciated that signal strength will diminish significantly as the distance between the launching device (10) and the target device (20) increases. This distance is in part determined by the amount of intervening tissue (34) between the two devices. By way of example, if the signal (40) is an ultrasound signal, it can be expected that significant deterioration of signal will occur where the launching device (10) and the target device (20) a separated by more than around 20 mm of solid tissue. Obviously, the density of the intervening tissue (34) will also have an effect upon the deterioration of signal (40) over distance.

The frequency of the desired ultrasound signal also determines the thickness of the signal transducer, which for a standard ultrasound ceramic transducer—such as a PZT—will be 0.075 mm at 30 MHz.

Figure 2:
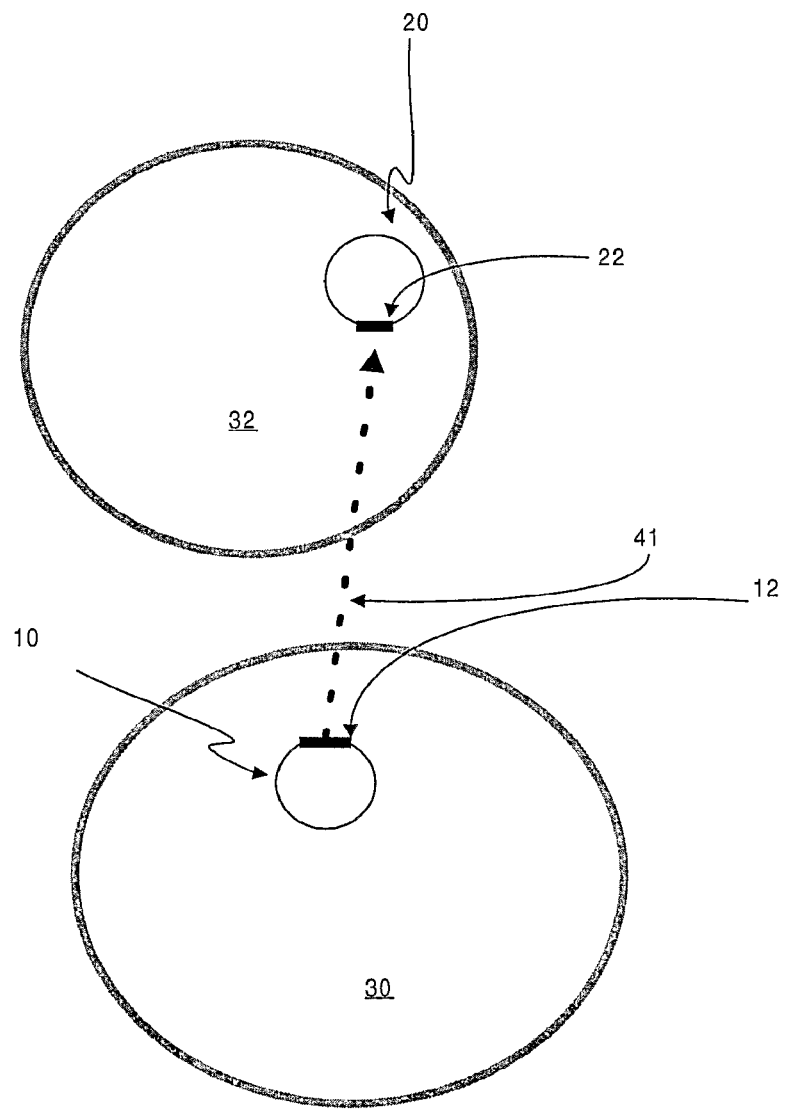
FIG. 2 is a cross sectional representation along the line of BB in FIG. 1.

FIG. 2 shows a cross sectional view of the arrangement in FIG. 1, along the line BB. The correct orientation of the launching device relative to the target device is an important factor as it is this line of orientation (41) that determines where the therapy is to be applied. It will be understood by the skilled addressee that the clinical need for precisional placing of therapy in a patient necessitates a requirement for a directional signal (40) that is linked to the means for delivering therapy. In this way, the user of the apparatus of the invention can administer therapy to the correct location by ensuring that the launching device (10) and the target device (20) are correctly positioned via transmission and reception of the signal (40). Hence, the orientation line (41) denotes not only the direction of signal travel but also the path along which therapy can be administered to the patient.

Figure 3:
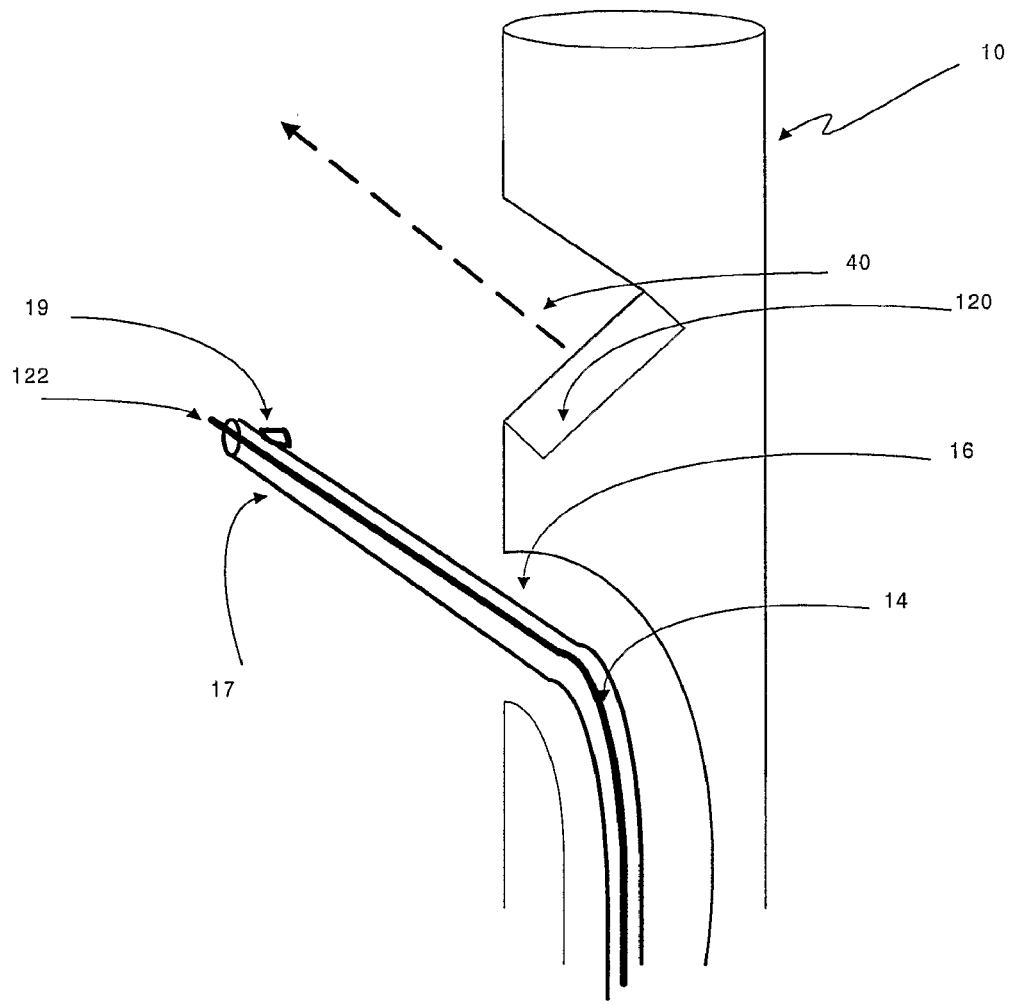
FIG. 3 is a representation of a specific embodiment of the launching device of the invention.

An embodiment of the invention is shown in FIG. 3 in which the signal transducer (120) is oriented at an oblique angle relative to the longitudinal axis of the launching device (10). Hence, the signal (40) is transmitted at an angle that is in the direction of forward travel of the launching device (10) as it enters a body cavity (30). The preferred signal beam angle is between around 20° and around 60° to the perpendicular, more preferably between around 30° and around 50° to the perpendicular, and most preferably around 45° to the perpendicular, when 0° corresponds to the longitudinal axis of the launching device in the direction of travel.

The launching device (10) in FIG. 2, also shows an embodiment of the invention in which one means for administering therapy is provided. Launching device (10) comprises a hollow needle or cannula (17). The hollow needle (17) is located in an undeployed or retracted state within the lumen (13) of launching device (10). The hollow needle (17) may be deployed/extended from the launching device (10) at a time deemed appropriate by the user of the apparatus, via an aperture (16) in the outer sheath (11), The aperture (16), thus, can allow communication between the lumen (13) and the body cavity (30). It should be noted that the hollow needle (17) preferably travels along a path that is parallel to the direction of the signal (40) and is used to pierce the intervening tissue (34). In a preferred embodiment of the invention, the hollow needle makes a transit across the entirety of the intervening tissue (34) and in doing so allows the launching device (10) to access the second body cavity (32). If desired, the pathway made by the hollow needle (17)

through the intervening tissue (34) can be subsequently widened to allow fluid communication between the first body cavity (30) and the second body cavity (32).

Therapeutic means suitable for use in the invention can comprise devices or instruments selected from the group consisting of a cannula; a laser; a radiation-emitting device; a probe; a drill; a blade; a wire; a needle and appropriate combinations thereof.

In a specific embodiment of the invention, the hollow needle (17) comprises a sensor (19) so as to assist further in determining positional information of the tip of the hollow needle relative to the launching device. In another specific embodiment of the invention the sensor (19) is capable of detecting changes in hydrostatic pressure. Other sensors that are suitable for use in the apparatus and methods of the invention can include temperature sensors, oxygenation sensors and/or colour sensors Optionally, the hollow needle can further comprise an additional signal transducer (122). In the embodiment shown in FIG. 3 the signal transducer (122) is located near the tip of the hollow needle on the end of a guide wire (14). However, the signal transducer (122) can easily be located on the hollow needle if this is preferred. In use, the signal transducer (122) is driven with a short transmit pulse which produces a non-directional signal pulse. The signal pulse can be detected by the receiving transducer (23) mounted on the target device (20). From the time delay between the transmit pulse to the receipt of the signal pulse on the receiving transducer (23) the distance from the incoming guide wire (14) or hollow needle (17) to the receiving transducer (23) and hence the target device (20), can be determined.

As mentioned above, the target device (20) comprises a receiving transducer (22) for receiving the signal (40). The receiving transducer (22) can be unidirectional—i.e. capable of receiving a signal from one direction only—or omnidirectional—i.e. capable of receiving a signal from any direction. In the embodiment of the invention shown in FIG. 4, a target device (20) is located within a body cavity (32). The target device (20) comprises an omnidirectional ultrasound signal receiving transducer. A reflecting cone (601) directs the signal (40) onto a disc-shaped receiving transducer (60). An acoustically transparent window (602) separates the reflecting cone (601) from the receiving transducer (60). In an alternative embodiment, an omnidirectional ultrasound signal receiving transducer can be obtained by locating cylinder of a flexible piezoelectric material such as PVDF (polyvinyldifluoride) around the outer sheath of the target device (20). In such a way the cylinder acts in an equivalent manner to the receiving transducer (60).

Figure 4:
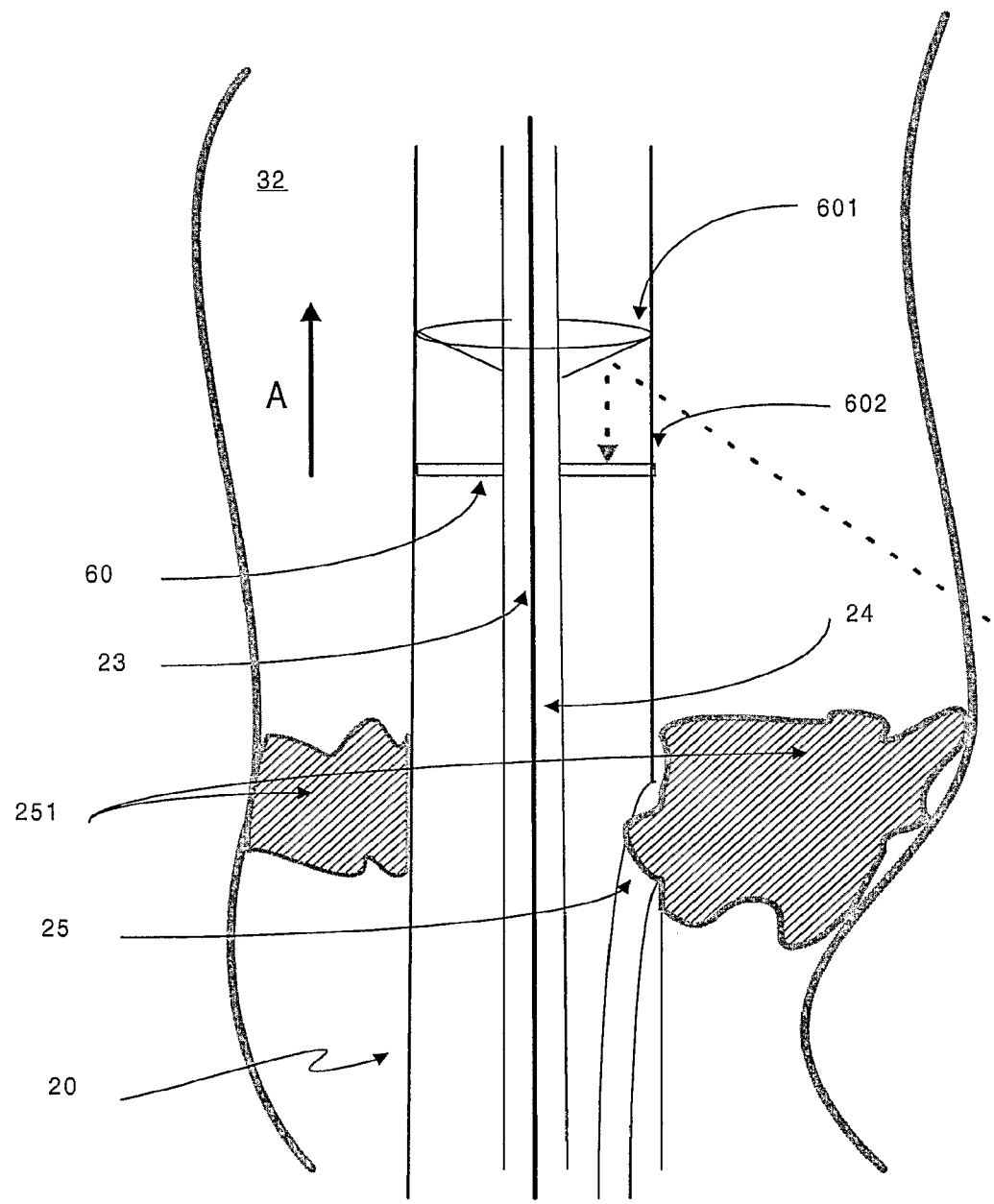
FIG. 4 is a representation of a specific embodiment of the target device of the invention. Arrow A shows the reversed direction of blood flow after an arterial-venous stenosis (also called PICVA) has been effected.

FIG. 4 also shows an embodiment of the invention in which the target device (20) comprises a channel (25) for administering an agent, such as a therapeutic agent, to a patient. In a specific embodiment, the channel (25) functions as a conduit to allow application of a blocking material (251) that serves to obstruct or occlude the body cavity (32). The blocking material (251) can be suitably selected from a gel based substance. The placement of the blocking material (251) can be directed by movement of the target device (20). The presence of a guide member (24) within the lumen (23) of the target device (20) allows the user of the apparatus to precisely manipulate the position of the target device (20) as required. Alternative blocking materials (251) can include embolisation members (such as balloons) and self-expanding stents, for example.

The launching device (10) comprises a signal transducer (12) that is optionally oriented so that the signal (40) is transmitted at an angle as shown in FIG. 2. In an alternative embodiment of the invention, shown in FIG. 5, the signal transducer is in the form of a signal transducer array (123). The signal transducer array (123) comprises a plurality of signal transducer elements (124) which can be oriented collectively and thereby define the signal beam width and angle relative to the launching device (10). A further advantage of the embodiment shown in FIG. 5, is that the smaller size of the elements (124) means that the signal transducer does not occupy a significant proportion the lumen (13) of the launching device (10).

Figure 5:
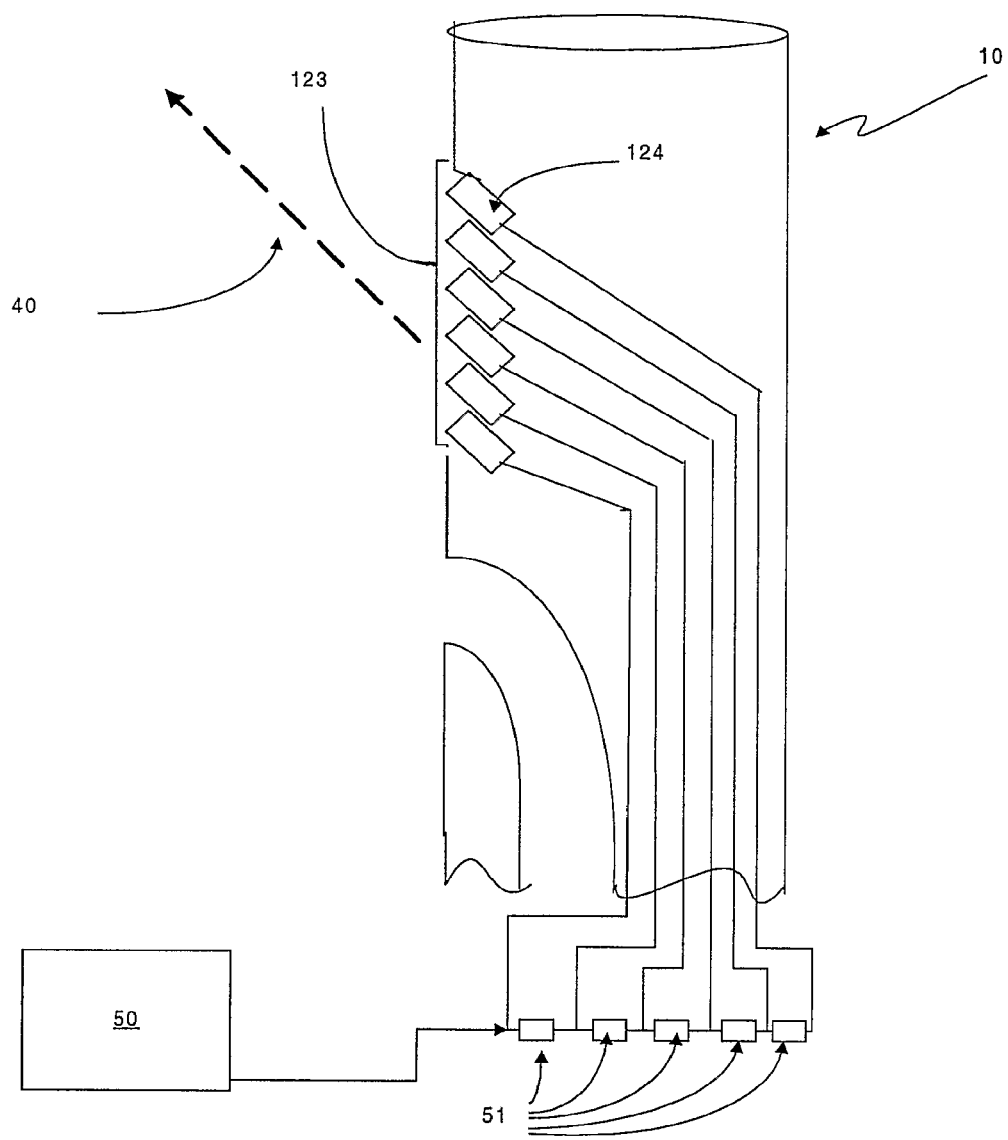
FIG. 5 is a representation of a specific embodiment of the launching device of the invention in which the signal transducer is comprised of an array of signal transducer elements.

The embodiment in FIG. 5 is particularly suited to ultrasound beam-forming signalling. FIG. 5 shows an array of signal transducer elements (124) that are separately connected to the transmitter (50) via delays (51) so that the signals to each element are delayed relative to each other. The delays ensure that the ultrasound wavefronts from each element are aligned to produce a beam of ultrasound (40) at the requisite angle. In an alternative embodiment where the signal (40) is in the form of visible light, an array of LEDs can be used.

Figure 6:
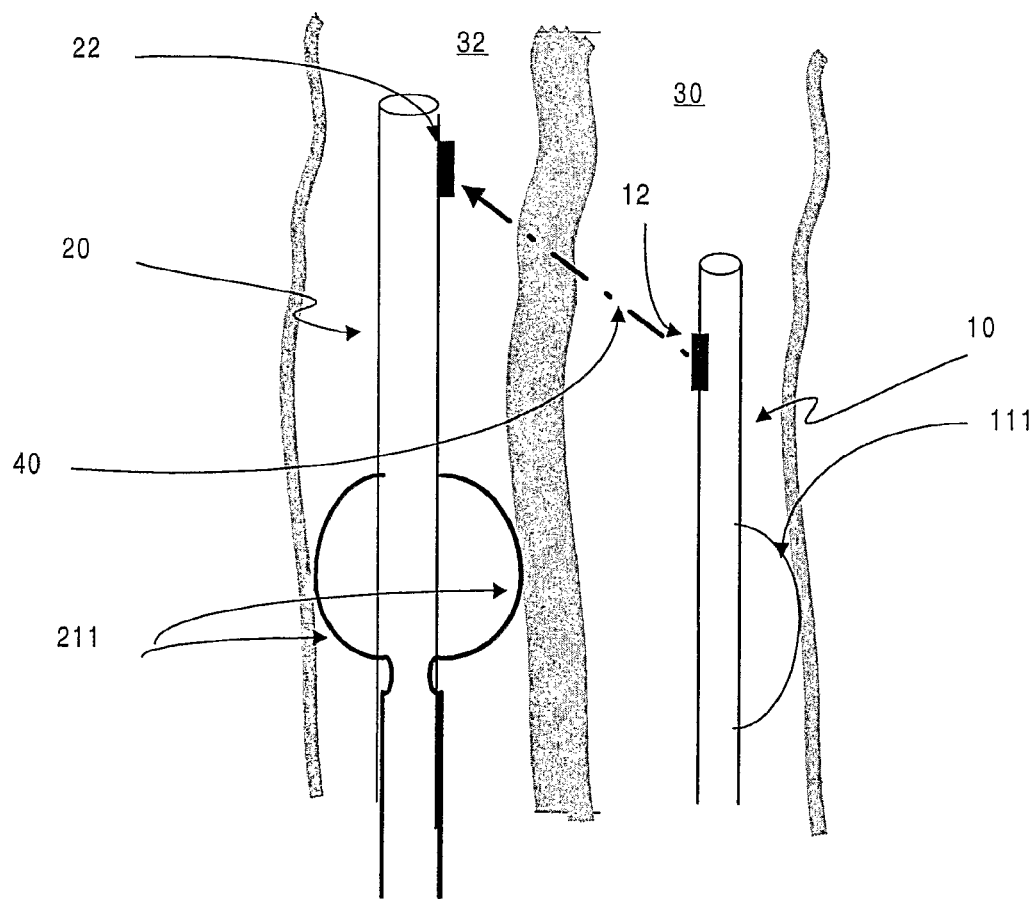
FIG. 6 is a representation of an embodiment of the invention wherein the launching and target devices comprise centring means.

To assist in the process of alignment between the launching device (10) in the first body cavity (30) and the target device (20) in the second body cavity (32), a further embodiment of the invention provides for the devices to comprise means for centring the respective devices within the body cavities. In one embodiment the centring means comprises an inflatable bladder or balloon (111) which is located in the lumen (13, 23) when in an undeployed state and, when the device (10, 20) reaches the desired location within the patient, can be inflated. The balloon (111) can be annular in shape such that is surrounds the device (10, 20) in a doughnut-like fashion. The balloon (111) can also be arranged such that it inflates on only one or on two opposite sides of the device. In FIG. 6, an embodiment of the invention is shown where the balloon (111) is shown deploying on one side of the launching device (10).

Alternatively, in a further embodiment, the centring means is comprised of one or more loop structures (211). In this embodiment, the one or more loop structures (211) are located either in the lumen (13, 23) or within recesses made in the outer sheath (11, 21) when in an undeployed or retracted state. Hence, when the device (10, 20) reaches the desired location within the patient, the one or more loop structures (211) can be expanded outwardly from the device (10, 20), thereby, centring the device (10, 20) within the body cavity (30, 32). Outward expansion of the loop structures (211) can be suitably effected by compression of a length of wire, for example, such that it bows outwardly from the outer sheath (11, 21). A centring device that adopts this conformation typically comprises a plurality of compressible lengths of wire, or other suitable flexible material, arranged in parallel at radially spaced intervals around the periphery of the outer sheath (11, 21). Compression of the plurality of wires can be induced by way of a sliding member (not shown) located proximally and/or distally near to the ends of the plurality of wires. The sliding member is capable of translational movement along the longitudinal axis of the device (10, 20).

In FIG. 6, an embodiment of the invention is shown where the target device (20) comprises fully deployed centring means (211) that has allowed the target device (20) to be centred within the body cavity (32). Arrangements for centring the devices within the body cavities include, but are not limited to, expandable Chinese-lantern type devices, reversibly expandable stents, coils, helices and retractable probes or legs.

The invention is further illustrated by the following non-limiting example.

EXAMPLE

The methods and apparatus of the present invention demonstrate particular utility in cardio-vascular surgery. In the present example the apparatus of the invention is used by a clinician to perform the procedure of arterial-venous stenosis (PICVA) so as to enable retroperfusion of cardiac tissue following occlusion of a coronary artery.

The launching catheter (10) is inserted into the occluded coronary artery by standard keyhole surgical techniques. Likewise, the target catheter (20) is inserted into the coronary vein that runs parallel to the coronary artery. The coronary vein is not occluded and, therefore, provides an alternative channel for blood flow to the cardiac muscle effectively allowing the occlusion in the coronary artery to be bypassed.

The launching catheter (10) comprises a PZT ultrasound transducer (12) (CTS Piezoelectric Products, Albuquerque, N. Mex.) that is oriented such that a directional ultrasound beam is transmitted at a 45° angle (relative to the longitudinal axis of the launching device) in the direction of blood flow in the artery. The ultrasound transducer (12) is activated and a 30 MHz directional ultrasound signal (40) is transmitted from the launching catheter (10). The target catheter (20) comprises an omnidirectional ultrasound receiving transducer (60). To assist with localisation of both the launching and target catheters (10, 20), both catheters comprise centring means in the form of an annular inflatable balloon (111). The centring means on the launching catheter (10) is deployed by the clinician when the launching catheter (10) is deemed to be in an appropriate location close to the site of the occlusion within the coronary artery. This is typically determined via standard fluoroscopic imaging techniques. The target catheter (20) is then moved within the adjacent coronary vein until the directed ultrasound signal (40) is detected by the signal receiving transducer (60). To enable more precise alignment between the launching and target catheters (10, 20) the centring means (111) on the target catheter (20) can be deployed either before or after the signal (40) is detected.

On reception of the transmitted signal (40) the clinician can be certain that the launching and target catheters (10, 20) are correctly located within their respective blood vessels to allow for the arterial-venous stenosis procedure to commence. The target catheter (20) is used to block blood flow within the coronary vein via administration of a gel blocking material (251) though a channel (25) in the target catheter (10). The blocking material (251) is administered at a position downstream in terms of the venous blood flow relative to the location of the receiving signal transducer (60).

The clinician is then able to initiate arterial-venous stenosis by deploying a hollow needle (17) from the launching catheter (10) substantially along a path that is parallel and close to that taken by the ultrasound signal (40) though the intervening tissue (34) between the coronary artery and the coronary vein. The hollow needle (17) comprises a sensor means (19) near its tip that detects changes in hydrostatic pressure. Hence, the clinician is able to monitor the transition from arterial pressure to venous pressure as the hollow needle passes between the two vessels. The hollow needle (17) further comprises a guide member (14) in the form of a wire located in the bore of the needle. Once the hollow needle has been passed across the intervening tissue (34) it is retracted leaving the guide wire (14) in place. Alternatively, once the hollow needle (17) has made the transition across the intervening tissue (34) the clinician is able to pass the guide wire (14) through the bore of the needle and then retract the needle (17) into the launching catheter (10).

Figure 7:
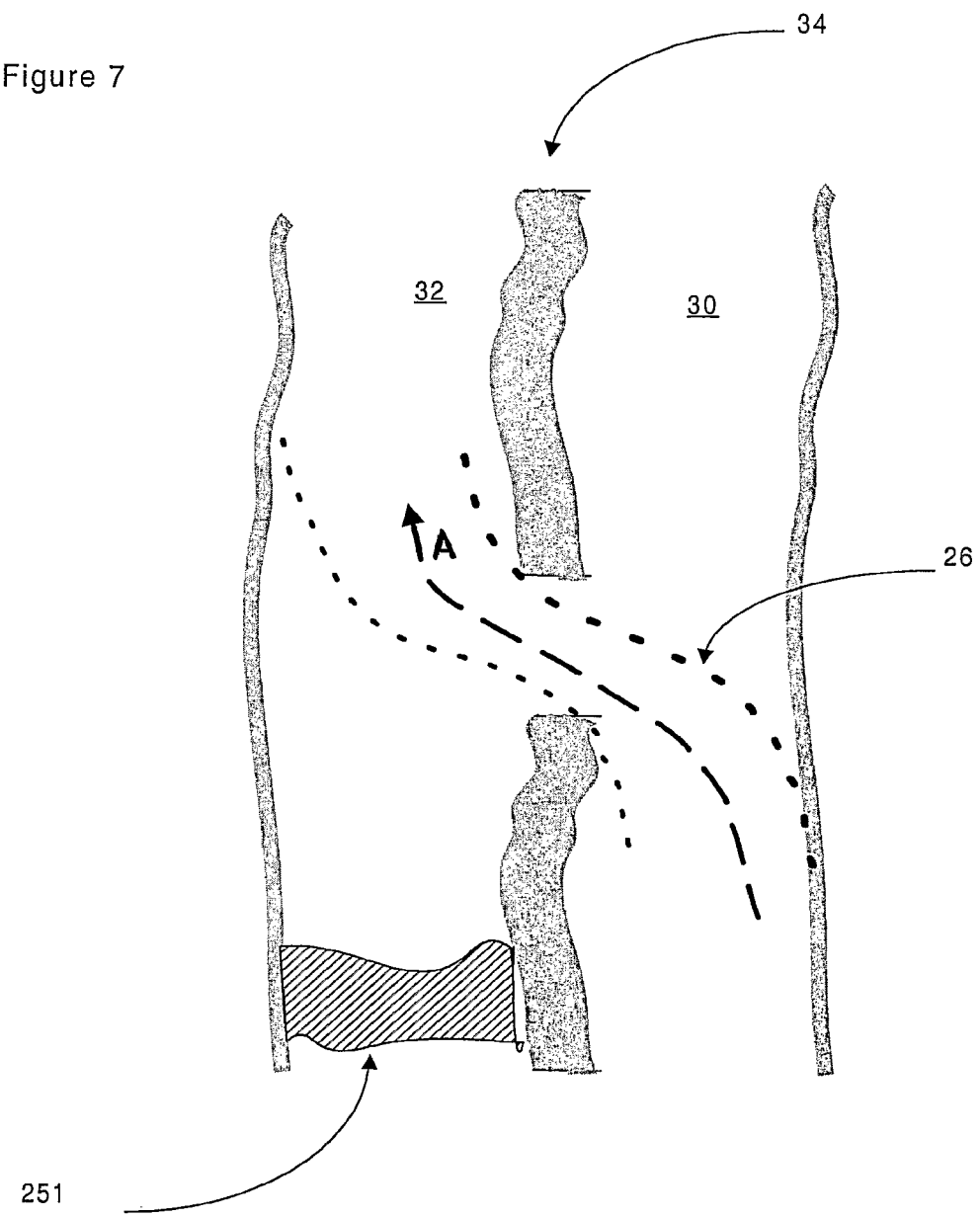
FIG. 7 is a representation of a stent in place following a procedure such as arterial-venous stenosis. Interrupted arrow A shows the direction of blood flow through the stent between the first and second body cavities.

The clinician withdraws the launching catheter (10) from the patient leaving the guide wire (14) in place. A further catheter device is then slid along the guide wire (14) and an expandable stent (26) is deployed in order to widen the perforation in the intervening tissue (34) between the coronary artery and vein (see FIG. 7). The target catheter (20) is withdrawn from the patient leaving the blocking material (251) in position. Optionally, a further block or suture may be inserted into the coronary vein prevent reversal of arterial blood flow.

Hence, arterial blood is thereby diverted into the venous system and is enabled to retroperfuse the cardiac muscle tissue.

Whilst the specific example described above is restricted to the field of cardio-vascular surgery, it is envisaged that the present method and apparatus could have far reaching applications in other forms of surgery. For example, any surgery involving the need to direct therapy from one body cavity towards another adjacent body cavity could be considered. Hence, the present invention finds ready applications in the fields of neurosurgery, urology and general vascular surgery. In addition the type of therapy need not be restricted to formation of channels between body cavities. For instance, the apparatus and methods described herein are also of use in directing techniques such as catheter ablation, non-contact mapping of heart chambers and the delivery of medicaments to precise areas of the body.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

NUMERALS USED IN THE FIGURES

| | |
|---|---|
| 10 | Launching device |
| 11 | Outer sheath |
| 111 | Centring device |
| 12 | Signal transducer |
| 120 | Angled signal transducer |
| 122 | Needle mounted signal transducer |
| 123 | Signal transducer array |
| 124 | Signal transducer element |
| 13 | Lumen |
| 14 | Guide means |
| 16 | Aperture |
| 17 | Hollow needle |
| 19 | Pressure sensor |
| 20 | Target device |
| 21 | Outer sheath |
| 211 | Centring device |
| 22 | Receiving transducer |
| 23 | Lumen |
| 24 | Guide member |
| 25 | Channel |
| 251 | Blocking material |
| 26 | Stent |
| 30 | First body cavity |
| 32 | Second body cavity |
| 34 | Intervening tissue |

| | |
|---|---|
| 40 | Signal |
| 41 | Orientation direction |
| 50 | Signal transmitter |
| 51 | Transmitter delay |
| 60 | Signal detector |
| 601 | Reflecting cone |
| 602 | window |
| 61 | Output display |

The invention claimed is:

1. A system for treating vasculature by forming a fistula, the system comprising:
 a launching catheter configured to be inserted in a stenosed artery, the launching catheter comprising:
  a longitudinal axis;
  an ultrasound signal transducer mounted at a non-parallel angle relative to the longitudinal axis, the ultrasound signal transducer configured to transmit an ultrasound signal at the non-parallel angle and along a directional path in a cone having position uncertainty less than 5 mm, the ultrasound signal configured to penetrate tissue outside the stenosed artery,
  an outer sheath,
  a lumen within the outer sheath,
  an aperture in the outer sheath, the aperture proximal to the ultrasound signal transducer, the aperture in communication with the lumen, and
  a needle deployable from inside the lumen to outside the lumen through the aperture and along a deployment path that is aligned with the directional path of the ultrasound signal; and
 a target catheter configured to be in a vein, the target catheter comprising:
  an omnidirectional ultrasound signal receiving transducer, and
  a reflecting cone configured to direct the ultrasound signal onto the omnidirectional ultrasound signal receiving transducer, wherein detection of the ultrasound signal by the omnidirectional ultrasound signal receiving transducer indicates that deploying the needle will exit the stenosed artery, traverse tissue between the stenosed artery and the vein, and will enter the vein.

2. The system of claim 1, wherein the needle comprises a needle lumen.

3. The system of claim 1, wherein the deployment path is parallel to the directional path.

4. The system of claim 1, wherein the non-parallel angle is between 20° and 60° where 0° is parallel to the longitudinal axis of the launching catheter.

5. The system of claim 1, wherein the needle comprises a sensor configured to detect a change in at least one of the group consisting of: hydrostatic pressure, temperature, oxygenation, or color.

6. The system of claim 1, wherein the deployment path is parallel to the directional path,
 wherein the non-parallel angle is between 20° and 60° where 0° is parallel to the longitudinal axis of the launching catheter, and
 wherein the needle comprises:
  a needle lumen, and
  a sensor configured to detect a change in at least one of the group consisting of: hydrostatic pressure, temperature, oxygenation, or color.

7. A system for treating vasculature by forming a fistula, the system comprising:
 a first catheter configured to be in an artery, the first catheter comprising:
  a longitudinal axis;
  an ultrasound signal transducer mounted at a non-parallel angle relative to the longitudinal axis of the first catheter, the ultrasound signal transducer configured to transmit an ultrasound signal at the non-parallel angle and along a directional path, the ultrasound signal configured to penetrate tissue outside the artery,
  a lumen, and
  a needle deployable from inside the lumen to outside the lumen along a deployment path that is oriented with the directional path of the ultrasound signal, the needle comprising a needle lumen; and
 a second catheter configured to be inserted in a vein, the second catheter comprising an ultrasound signal receiving transducer, wherein detection of the ultrasound signal by the ultrasound signal receiving transducer indicates that deploying the needle along the deployment path will cause the needle to enter the vein.

8. The system of claim 7, wherein the needle comprises a needle lumen.

9. The system of claim 7, wherein the non-parallel angle is between 20° and 60° where 0° is parallel to the longitudinal axis of the first catheter.

10. The system of claim 7, wherein the first catheter comprises a needle exit point proximal to the ultrasound signal transducer.

11. The system of claim 7, wherein the needle comprises a sensor configured to detect a change in at least one of the group consisting of: hydrostatic pressure, temperature, oxygenation, or color.

12. The system of claim 7, wherein the non-parallel angle is between 20° and 60° where 0° is parallel to the longitudinal axis of the first catheter,
 wherein the first catheter comprises a needle exit point proximal to the ultrasound signal transducer, and
 wherein the needle comprises:
  a needle lumen, and
  a sensor configured to detect a change in at least one of the group consisting of: hydrostatic pressure, temperature, oxygenation, or color.

13. A system for treating vasculature by forming a fistula, the system comprising:
 a first catheter configured to be in a first anatomical cavity, the first catheter having a longitudinal axis, the first catheter comprising:
  an ultrasound signal transducer mounted at a non-parallel angle relative to the longitudinal axis of the first catheter, the ultrasound signal transducer configured to transmit an ultrasound signal at the non-parallel angle and along a directional path, the ultrasound signal configured to penetrate tissue outside the first anatomical cavity,
  a lumen, and
  a needle deployable from inside the lumen to outside the lumen along a needle track that is parallel to the directional path of the ultrasound signal; and
 a second catheter configured to be inserted in a second anatomical cavity different than the first anatomical cavity, the second catheter comprising an ultrasound signal receiving transducer.

14. The system of claim 13, wherein detection of the ultrasound signal by the ultrasound signal receiving transducer indicates that deploying the needle will enter the second anatomical cavity.

15. The system of claim 13, wherein the needle comprises a needle lumen.

16. The system of claim 13, wherein the non-parallel angle is between 20° and 60° where 0° is parallel to the longitudinal axis of the first catheter.

17. The system of claim 13, wherein the first catheter comprises an aperture proximal to the ultrasound signal transducer.

18. The system of claim 13, wherein the needle comprises a sensor configured to detect a change in at least one of the group consisting of: hydrostatic pressure, temperature, oxygenation, or color.

19. The system of claim 13, wherein detection of the ultrasound signal by the ultrasound signal receiving transducer indicates that deploying the needle will enter the second anatomical cavity, and wherein the first catheter comprises an aperture proximal to the ultrasound signal transducer, and wherein the aperture is in communication with the lumen.

\* \* \* \* \*